(12) United States Patent
Gorin et al.

(10) Patent No.: US 10,288,630 B2
(45) Date of Patent: May 14, 2019

(54) BLOOD TESTING SYSTEM AND METHOD

(71) Applicant: C A Casyso GmbH, Basel (CH)

(72) Inventors: Michael Gorin, Incline Village, NV (US); Robert S. Hillman, San Diego, CA (US); Cory Lee McCluskey, Encinitas, CA (US); Hubert Martin Schwaiger, Munich (DE)

(73) Assignee: C A Casyso GmbH, Basel (CH)

( * ) Notice: Subject to any disclaimer, the term of this patent is extended or adjusted under 35 U.S.C. 154(b) by 626 days.

(21) Appl. No.: 14/958,876

(22) Filed: Dec. 3, 2015

(65) Prior Publication Data

US 2016/0091514 A1    Mar. 31, 2016

Related U.S. Application Data

(63) Continuation-in-part of application No. 14/500,248, filed on Sep. 29, 2014.

(51) Int. Cl.
| | | |
|---|---|---|
| *G01N 33/86* | (2006.01) | |
| *G01N 11/14* | (2006.01) | |
| *G01N 33/49* | (2006.01) | |

(52) U.S. Cl.
CPC ............ *G01N 33/86* (2013.01); *G01N 11/14* (2013.01); *G01N 33/4905* (2013.01)

(58) Field of Classification Search
CPC ..... B01L 2200/0621; B01L 2200/0684; B01L 2200/10; B01L 2300/0627; B01L 2300/087; B01L 2400/049; B01L 2400/0694; B01L 3/502; B01L 3/561; B01L 3/567; G01N 11/00; G01N 33/4905; G01N 33/86
See application file for complete search history.

(56) References Cited

U.S. PATENT DOCUMENTS

| | | |
|---|---|---|
| 2,555,937 A | 6/1951 | Rosenthal |
| 2,995,425 A | 8/1961 | Fuhrmann |
| 3,714,815 A | 2/1973 | Hartert et al. |
| 3,803,903 A | 4/1974 | Lin |
| 3,903,903 A | 9/1975 | Matsumura |
| 4,148,216 A | 4/1979 | Do et al. |
| 4,193,293 A | 3/1980 | Cavallari |
| D260,428 S | 8/1981 | Fekete |
| 4,319,194 A | 3/1982 | Cardinal |
| 4,599,219 A | 7/1986 | Cooper |
| 4,726,220 A | 2/1988 | Feier et al. |

(Continued)

FOREIGN PATENT DOCUMENTS

| | | |
|---|---|---|
| CN | 1853104 | 10/2006 |
| CN | 101195112 A | 6/2008 |

(Continued)

OTHER PUBLICATIONS

Chinese Office Action (OA) for App. No. 200980151858.5 dated May 21, 2013, 16 pgs.

(Continued)

*Primary Examiner* — Samuel P Siefke
(74) *Attorney, Agent, or Firm* — Fenwick & West LLP

(57) ABSTRACT

Some embodiments of a blood coagulation testing system include an analyzer console device and a single-use cartridge component configured to releasably install into the console device. In some embodiments, the blood coagulation testing system can operate as an automated thromboelastometry system that is particularly useful, for example, at a point-of-care site.

30 Claims, 17 Drawing Sheets

(56) References Cited

U.S. PATENT DOCUMENTS

| | | |
|---|---|---|
| 4,752,449 A | 6/1988 | Jackson et al. |
| 4,753,776 A | 6/1988 | Hillman et al. |
| 4,756,884 A | 7/1988 | Hillman et al. |
| 4,765,180 A | 8/1988 | Clifton |
| 4,767,600 A | 8/1988 | Vicario |
| D302,294 S | 7/1989 | Hillman |
| 4,868,129 A | 9/1989 | Gibbons et al. |
| D305,360 S | 1/1990 | Fechtner |
| 4,948,961 A | 8/1990 | Hillman et al. |
| 4,956,089 A | 9/1990 | Hurst |
| 4,963,498 A | 10/1990 | Hillman et al. |
| 5,009,316 A | 4/1991 | Klein |
| 5,028,142 A | 7/1991 | Ostoich et al. |
| 5,077,017 A | 12/1991 | Gorin et al. |
| 5,104,813 A | 4/1992 | Besemer et al. |
| D327,743 S | 7/1992 | Frenkel et al. |
| 5,164,598 A | 11/1992 | Hillman et al. |
| 5,207,988 A | 5/1993 | Lucas |
| 5,222,808 A | 6/1993 | Sugarman et al. |
| 5,223,219 A | 6/1993 | Subramanian et al. |
| 5,223,227 A | 6/1993 | Zuckerman |
| 5,287,732 A | 2/1994 | Sekiguchi |
| D347,067 S | 5/1994 | Shartle et al. |
| 5,447,440 A | 9/1995 | Davis et al. |
| 5,531,102 A | 7/1996 | Brookfield et al. |
| 5,777,212 A | 7/1998 | Sekiguchi et al. |
| 5,777,215 A | 7/1998 | Calatzis et al. |
| 5,788,928 A | 8/1998 | Carey et al. |
| 5,902,937 A | 5/1999 | Amrani et al. |
| 6,012,712 A | 1/2000 | Bernstein |
| 6,066,243 A | 5/2000 | Anderson et al. |
| 6,200,532 B1 | 3/2001 | Wu |
| 6,448,024 B1 | 9/2002 | Bruegger |
| 6,537,819 B2 | 3/2003 | Cohen |
| 6,613,286 B2 | 9/2003 | Braun et al. |
| D481,133 S | 10/2003 | Blouin et al. |
| D482,454 S | 11/2003 | Gebrian |
| 6,662,031 B1 | 12/2003 | Khalil et al. |
| 6,699,718 B1 | 3/2004 | Bruegger |
| 6,750,053 B1 | 6/2004 | Opalsky |
| 6,838,055 B2 | 1/2005 | Sando et al. |
| 6,942,836 B2 | 9/2005 | Freudenthal et al. |
| 6,951,127 B1 | 10/2005 | Bi |
| 7,399,637 B2 | 7/2008 | Wright et al. |
| 7,412,877 B1 | 8/2008 | Bi |
| 7,422,905 B2 | 9/2008 | Clague |
| 7,491,175 B2 | 2/2009 | Ruether et al. |
| 7,497,997 B2 | 3/2009 | Glezer et al. |
| 7,524,670 B2 | 4/2009 | Cohen et al. |
| 7,595,169 B2 | 9/2009 | Swaim et al. |
| 7,732,213 B2 | 6/2010 | Cohen et al. |
| 7,745,223 B2 | 6/2010 | Schubert et al. |
| 7,811,792 B2 | 10/2010 | Cohen et al. |
| 7,901,629 B2 | 3/2011 | Calatzis et al. |
| 7,947,505 B2 | 5/2011 | Kawasaki et al. |
| 7,951,606 B2 | 5/2011 | Pei et al. |
| 8,003,401 B2 | 8/2011 | Tonnessen et al. |
| D645,973 S | 9/2011 | Hoenes |
| 8,110,392 B2 | 2/2012 | Battrell et al. |
| 8,168,442 B2 | 5/2012 | Petersen et al. |
| 8,383,045 B2 | 2/2013 | Schubert et al. |
| 8,448,499 B2 | 5/2013 | Schubert et al. |
| 8,857,244 B2 | 10/2014 | Schubert et al. |
| 9,061,280 B2 | 6/2015 | Tanaami et al. |
| D737,993 S | 9/2015 | Tan et al. |
| 9,272,280 B2 | 3/2016 | Viola et al. |
| 9,285,377 B2 | 3/2016 | Schubert et al. |
| D777,343 S | 1/2017 | Gorin et al. |
| 2002/0081741 A1 | 6/2002 | Braun, Sr. |
| 2002/0177958 A1 | 11/2002 | Widrig Opalsky et al. |
| 2003/0073244 A1 | 4/2003 | Cohen et al. |
| 2004/0131500 A1 | 7/2004 | Chow |
| 2005/0136541 A1 | 6/2005 | De Haan |
| 2005/0233460 A1 | 10/2005 | Clague et al. |
| 2005/0233466 A1 | 10/2005 | Wright et al. |
| 2007/0059840 A1 | 3/2007 | Cohen et al. |
| 2007/0140902 A1 | 6/2007 | Calatzis et al. |
| 2007/0243105 A1 | 10/2007 | Kratzer et al. |
| 2008/0026476 A1 | 1/2008 | Howell et al. |
| 2008/0160500 A1 | 7/2008 | Fuller |
| 2008/0194041 A1 | 8/2008 | Guirguis |
| 2008/0227217 A1 | 9/2008 | Yamamoto et al. |
| 2008/0251383 A1 | 10/2008 | Sobek et al. |
| 2008/0261261 A1 | 10/2008 | Grimes et al. |
| 2008/0297169 A1 | 12/2008 | Greenquist et al. |
| 2009/0130645 A1 | 5/2009 | Schubert et al. |
| 2010/0154520 A1 | 6/2010 | Schubert |
| 2010/0184201 A1 | 7/2010 | Schubert et al. |
| 2011/0237913 A1 | 9/2011 | Schubert et al. |
| 2011/0252352 A1 | 10/2011 | Viola et al. |
| 2012/0294767 A1 | 11/2012 | Viola et al. |
| 2013/0270113 A1 | 10/2013 | Huang |
| 2013/0323846 A1 | 12/2013 | Schubert et al. |
| 2013/0323847 A1 | 12/2013 | Schubert et al. |
| 2013/0323848 A1 | 12/2013 | Schubert et al. |
| 2013/0333448 A1 | 12/2013 | Schubert et al. |
| 2014/0004613 A1 | 1/2014 | Goldstein |
| 2014/0271409 A1 | 9/2014 | Knight et al. |
| 2015/0253271 A1 | 9/2015 | Giridhar et al. |
| 2016/0091483 A1 | 3/2016 | McCluskey |
| 2016/0091511 A1 | 3/2016 | Di Tullio et al. |
| 2016/0091515 A1 | 3/2016 | Gorin |
| 2016/0091516 A1 | 3/2016 | Gorin |
| 2016/0091517 A1 | 3/2016 | Gorin |
| 2016/0195557 A1 | 7/2016 | Schubert et al. |
| 2016/0313357 A1 | 10/2016 | Viola et al. |
| 2016/0361715 A1 | 12/2016 | Shi et al. |
| 2016/0377638 A1 | 12/2016 | Bels et al. |

FOREIGN PATENT DOCUMENTS

| | | |
|---|---|---|
| CN | 101301632 A | 11/2008 |
| CN | 102265151 A | 11/2011 |
| DE | 2740932 A1 | 11/1978 |
| DE | 10135569 A1 | 2/2003 |
| DE | 202014002289 | 9/2014 |
| EP | 0404456 A2 | 12/1990 |
| EP | 1367392 A1 | 12/2003 |
| EP | 1394546 A1 | 3/2004 |
| EP | 1627725 A2 | 2/2006 |
| EP | 1884778 A1 | 2/2008 |
| EP | 1901065 | 3/2008 |
| EP | 2208996 | 9/2010 |
| EP | 2202517 | 8/2012 |
| GB | 2257256 A | 1/1993 |
| JP | 1971-004947 | 11/1971 |
| JP | 1987-140047 | 6/1987 |
| JP | 1991-031764 | 2/1991 |
| JP | 1997-159596 | 6/1997 |
| JP | 09-507580 A | 7/1997 |
| JP | 2001-516880 A | 10/2001 |
| JP | 2006-053142 A | 2/2006 |
| JP | 2010-266453 A | 11/2010 |
| JP | 2011-174952 A | 9/2011 |
| JP | 2012-513582 A | 6/2012 |
| JP | 2012-515340 | 7/2012 |
| JP | 2015-045642 | 3/2015 |
| WO | WO 1989/006803 A1 | 7/1989 |
| WO | 200250535 | 6/2002 |
| WO | WO 2002/063273 A2 | 8/2002 |
| WO | WO 2005/106467 A1 | 11/2005 |
| WO | WO 2006/091650 A2 | 8/2006 |
| WO | WO 2006/126290 A1 | 11/2006 |
| WO | WO 2007/047961 A2 | 4/2007 |
| WO | 2008075181 | 6/2008 |
| WO | 2010072620 | 7/2010 |
| WO | WO 2010/072620 A1 | 7/2010 |
| WO | WO 2008/093216 A1 | 8/2011 |
| WO | WO 2011/117017 A1 | 9/2011 |
| WO | WO 2013/172003 A1 | 11/2013 |

(56) References Cited

FOREIGN PATENT DOCUMENTS

| WO | 2014103744 | 7/2014 |
|---|---|---|
| WO | 2014115478 | 7/2014 |

OTHER PUBLICATIONS

Chinese Office Action for App. No. 200980151858.5 dated Feb. 14, 2014, 4 pgs.

European Extended search report for App No. 13167983.9, dated Nov. 6, 2013, 3 pgs.

European Office Action for App. No. 08172769.5, dated Jun. 1, 2011, 12 pgs.

European Office Action for App. No. 12179576.9, dated May 22, 2013, 10 pgs.

European Office Action for App. No. 13167979.7, dated Nov. 15, 2016, 8pgs.

International Preliminary report on patentability for PCT/EP2009/067181, dated Jun. 29, 2011, 9 pgs.

International search report and written opinion for Ap. No. PCT/EP2009/067181, dated Mar. 22, 2010, 12 pgs.

Japanese notification of refusal for Ap. No. 2014-165975, dated Jul. 17, 2015, 8 pgs.

Korean Office Action for Ap. No. 1020117017187, dated Mar. 28, 2016, 11 pgs.

Korean Office Action for Application No. 1020167029191, dated Nov. 17, 2016, 5 pgs.

Notification of reasons for refusal for Ap. No. 2015-132034, dated Jul. 29, 2016, 5 pgs.

Rotem ® "Targeted therapy for coagulation management in patients with massive bleeding," https://www.heath.qld.gov.au/_data/assets/pdf_file/0023/427145/wp024.pdf, Nov. 2012, 30 pgs, [brochure].

"HealthPACT,""Rotational thromboelastometry (ROTEM)—targeted therapy for coagulation management in patitnets with massive bleeding," "Health Policy Advisory Committee on Technology. Retrieved from the Internet: <URL:https://www.heath.qld.gov.au/healthpact/docs/briefs/WP024.pdg>, 30 pages, Nov. 2012".

European Office Action for Application No. 13163014.7, dated Mar. 24, 2014, 12 pages.

Japanese Notification for Refusal for Application No. 2011-541392, dated Jun. 14, 2013, 4 pages.

International Search Report and Written Opinion, PCT Application No. PCT/US16/34501, Aug. 31, 2016, 17 pages.

PCT International Search Report and Written Opinion, PCT Application No. PCT/US2017/049505, Nov. 2, 2017, 17 pages.

Anonymous: Rotem delta Whole Blood Haemostasis System using Thromboelastometry US Operating Manual,: [retrieved on Oct. 30, 2015]. Retrieved from the internet: <URL: http://www.sfgh-poct.org/wp-content/uploads/2013/02/ROTEM-delta-US-Operating-Manual-Part-12.pdf>, Sep. 2012.

Lang et al., "Evaluation of the new device ROTEM platelet" [retrieved on Oct. 28, 2015]. Retrieved from the Internet: <URL: https://www.rotem.de/wp-content/uploads/2014-09-Lang-et-al-2014.pdf>, Jan. 1, 2014.

European Search Report and Opinion for Application No. 15187347.8, dated Jun. 1, 2016 (16 Pages).

PCT International Search Report and Written Opinion, PCT Application No. PCT/US16/64800, Feb. 16, 2017, 14 pages.

PCT International Search Report and Written Opinion, PCT Application No. PCT/US2016/064806, Feb. 15, 2017, 18 pages.

PCT International Search Report and Written Opinion, PCT Application No. PCT/US2016/064790, Feb. 15, 2017, 17 pages.

PCT International Search Report and Written Opinion, PCT Application No. PCT/US2016/064797, Feb. 15, 2017, 16 pages.

ROTEM® delta, "Targeted therapy stops the bleeding," 6 pages, Jan. 6, 2014, [brochure].

ROTEM® delta, "Whole Blood Haemostasis System using Thromboelastomerty Operating Manual," 164 pages, Nov. 17, 2014 [brochure].

Calatzis et al., "Strategies to Assess Individual Susceptibility to abciximab Therapy Using a New Functional Assay," Annals of Hematology, (Berlin, DE) vol. 76, No. Suppl 1, p. A61, XP009097526, 1998.

Chakroun et al., "The influence of fibrin polymerization and platelet-mediated contractile forces on citrated whole blood thromboelastography profile," Thromb Haemost., 95(5):822-828, May 2006.

Greilich et al., "Near-site monitoring of the antiplatelet drug abciximab using the Hemodyne analyzer and modified thrombelastograph," J Cardiothorac Vase Anesth., 13(1):58-64, Feb. 1999.

Hartert, "Blood Coagulation Studies with Thromboelastography—A New Research Method," Klin Wochenschrift 26:577-583, Oct. 1948 [English translation].

Kawasaki et al., "The effects of vasoactive agents, platelet agonists and anticoagulation on thrombelastography," ActaAnaesthesiol Scand., 51(9):1237-1244, Oct. 2007.

Khurana et al., "Monitoring platelet glycoprotein lib/Illa-fibrin interaction with tissue factor-activated thromboelastography," J Lab Clin Med., 130(4):401-411, Oct. 1997.

Nield et al., "MRI-based blood oxygen saturation measurements in infants and children with congenital heart disease," Pediatr Radiol., 32(7):518-522. Epub Apr. 16, 2002.

Nielsen et al., "Evaluation of the contribution of platelets to clot strength by thromboelastography in rabbits: the role of tissue factor and cytochalasin D," Anesth Anafa., 91(1):35-39, Jul. 2000.

Noon et al., "Reduction of blood trauma in roller pumps for long-term perfusion" World J Surg., 9(1):65-71, Feb. 1985.

Novotny et al., "Platelets secrete a coagulation inhibitor functionally and antigenically similar to the lipoprotein associated coagulation inhibitor," Blood, 72(6):2020-2025, Dec. 1988.

Prisco and Paniccia, "Point-of-Care Testing of Hemostasis in Cardiac Surgery", Thromb J., 1(1):1, May 6, 2003.

Rodzynek et al., "The transfer test: a new screening procedure for thrombotic diseases," J Surg Res., 35(3):227-233, Sep. 1983.

Rotem® "When Minutes Count to Stop the Bleeding," Pentapharm GmbH, www.rotem.de, 6 pages, Jun. 2007. [brochure].

Rugeri et al., "Diagnosis of early coagulation abnormalities in trauma patients by rotation thrombelastography," J Thromb Haemost., 5(2):289-295, Epub Nov. 16, 2006.

Salooia and Perrv, "Thrombelastography," Blood Coa1ml Fibrinolvsis, 12(5):327-37, Jul. 2001.

Shore-Lesserson et al., "Thromboelastography-guided transfusion algorithm reduces transfusions in complex cardiac surgery," Anesth Analg., 88(2):312-319, Feb. 1999.

Soria et al., "Fibrin stabilizing factor (F XIII) and collagen polymerization," Experientia, 31(11):1355-1357, Nov. 15, 1975.

Spannagl et al., "Point-of-Care Analysis of the Homostatic System," Laboratoriumsmedizin, (Kirchheim, DE), 26(1-2):68-76, Feb. 2002.

Srinivasa et al., "Thromboelastography: Where Is It and Where Is It Heading?" Int'l Anesthesiology Clinics, 39(1):35-49, Winter 2001.

Tanaka et al., "Thrombin generation assay and viscoelastic coagulation monitors demonstrate differences in the mode of thrombin inhibition between unfractionated heparin and bivalirudin," Anesth Analg., 105(4):933-939, Oct. 2007.

Japanese Office Action, Japanese Application No. 2015-191180, Nov. 17, 2017, 9 pages.

PCT International Search Report and Written Opinion, PCT Application No. PCT/US18/40120, Sep. 20, 2018, 13 pages.

First Office Action with concise explanation of relevance, Chinese Patent Application No. 201680074338.9, dated Feb. 3, 2019, 5 pages.

Partial European search report, European Patent Application No. 18193752.5, dated Feb. 12, 2019, 15 pages.

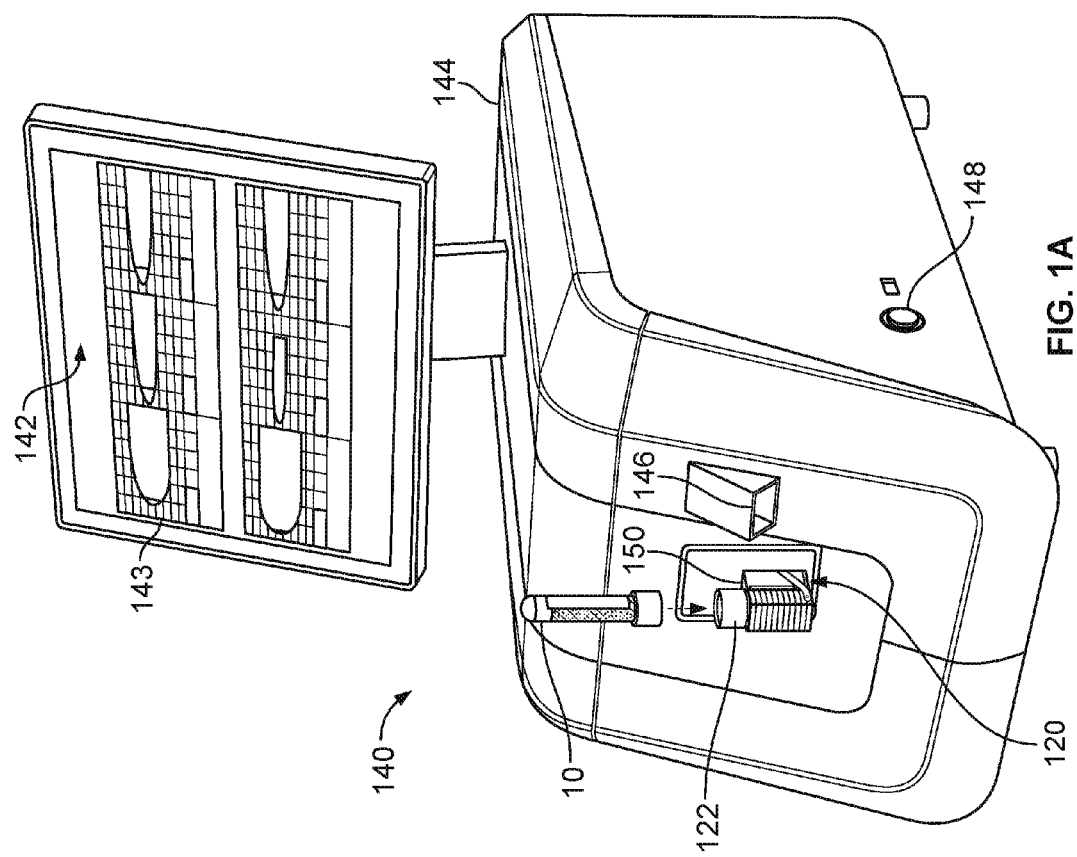
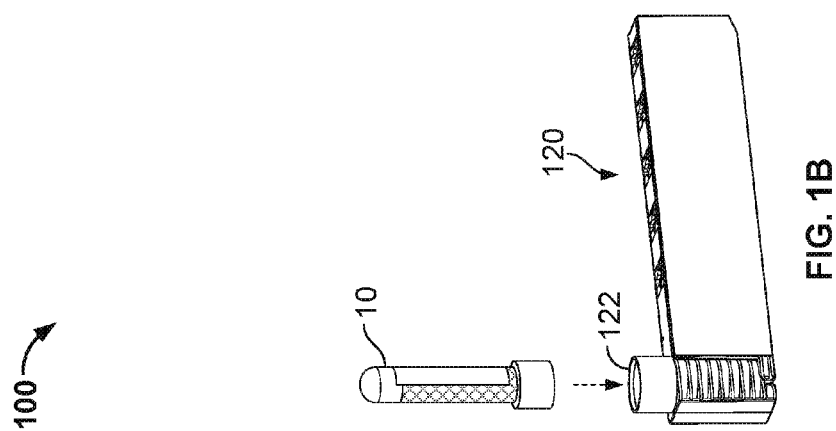

BLOOD TESTING SYSTEM AND METHOD

CROSS REFERENCE TO RELATED APPLICATIONS

The present application is a continuation in part of U.S. application Ser. No. 14/500,248, "Blood Testing System and Method," filed on Sep. 29, 2014, the entire disclosure of which is hereby incorporated by reference, in its entirety, for all purposes.

TECHNICAL FIELD

This document relates to systems and method for testing characteristics of a blood sample, such as an automated thromboelastometry system for point-of-care whole blood coagulation analysis.

BACKGROUND

Hemostasis is the human body's response to blood vessel injury and bleeding. Hemostasis involves a coordinated effort between platelets and numerous blood clotting proteins (or clotting factors), resulting in the formation of a blood clot and the subsequent stoppage of bleeding.

Various methods have been introduced to assess the potential of blood to form an adequate clot and to determine the blood clot's stability. Common laboratory tests such as thrombocyte counts or the determination of fibrin concentration provide information on whether the tested component is available in sufficient amount, but some of those tests might not answer the question of whether the tested component works properly under physiological conditions. Other laboratory tests work on blood plasma, which may impose additional preparation steps and additional time beyond what is preferred, for example, in the point-of-care context (e.g., in a surgical theater during a surgical operation).

Another group of tests to assess the potential of blood to form an adequate clot is known as "viscoelastic methods." In at least some viscoelastic methods, the blood clot firmness (or other parameters dependent thereon) is determined over a period of time, for example, from the formation of the first fibrin fibers until the dissolution of the blood clot by fibrinolysis. Blood clot firmness is a functional parameter which contributes to hemostasis in vivo, as a clot must resist blood pressure and shear stress at the site of vascular injury or incision. In many cases, clot firmness may result from multiple interlinked processes including coagulation activation, thrombin formation, fibrin formation and polymerization, platelet activation, and fibrin-platelet interaction.

To isolate and test particular functions of thrombocytes, fibrinogen, and other factors in a blood sample, reagent compounds can be mixed with the blood sample to activate or inhibit certain components in the blood sample. In some commercially available point-of-care blood testing systems, liquid reagents are injected into a disposable plastic cup containing a blood sample, and the cup is then engaged by the control console of the blood testing system to evaluate characteristics of the coagulation/clotting of the blood sample. As part of the test process, the system requires manual intervention by the operator for each of the assays, for example, when pipettes are used by an operator for the dispensing and measuring of the reagents, blood, and mixed samples.

SUMMARY

Some embodiments of a system for testing characteristics of a blood sample (which, as used herein, should be understood to include blood or derivatives of blood such as plasma) can include a cartridge configured to mate with a control console and receive a blood sample for a point-of-care whole blood coagulation analysis. In particular circumstances, the cartridge is configured to interact with the control console so as to perform a number of automated transport and testing operations on portions of the blood sample so as to provide reliable and prompt results indicative of a patient's blood characteristics at the point-of-care (e.g., while the patient is in a surgical room undergoing surgery). For example, the system can serve as an automated thromboelastometry system for providing detailed and prompt results of blood coagulation characteristics in response to receiving a cartridge (and blood sample at the cartridge) and an indication from an operator to begin the automated testing process.

In some embodiments, the thromboelastometry system includes a reusable analyzer console and one or more single-use cartridge components configured to mate with the console. In one example, to operate the thromboelastometry system, a user inserts the cartridge into the analyzer console and, when prompted by the analyzer console, inserts a blood collection tube (containing a whole blood sample) into a receiver portion of the cartridge. The user is then prompted a user interface of the analyzer console to initiate a number of automated blood transfer and testing operations. Thereafter, the analyzer console automatically performs (without requiring further user interaction with the cartridge or the blood sample) the testing and displays the results on a graphical display using qualitative graphical representations and quantitative parameters. In this particular example, no manual pipetting, mixing, or handling of reagents by the user is needed. In some embodiments, four or more assays are automatically performed on the blood sample using a single cartridge device. Such assays provide information on the whole kinetics of hemostasis, such as clotting time, clot formation, clot stability, and lysis; moreover, such information can be promptly output from a user interface of the system to provide reliable and prompt results indicative of a patient's blood characteristics at the point-of-care (e.g., while the patient is in a surgical room undergoing surgery).

Particular embodiments described herein include a cartridge for use with a blood testing console. The cartridge may include a blood sample receiver configured to receive a blood sample to be tested. The cartridge may also include one or more blood processing and testing paths. Each blood processing and testing path can receive a portion of the blood sample and may include a blood sample volume measurement chamber, a mixing chamber, and a viscoelastic blood testing chamber. The blood sample volume measurement chamber may be in fluid communication with the blood sample receiver, and the blood sample volume measurement chamber may a selected internal volume to contain a predetermined volume of blood sample from the blood sample container. The mixing chamber may be in fluid communication with the blood sample volume measurement chamber and with a reagent, and the mixing chamber may be configured to receive blood sample from the blood sample volume measurement chamber and mix the received blood with the reagent. The viscoelastic blood testing chamber may be configured to receive mixed blood and reagent from the mixing chamber for a viscoelastic test to be performed on the mixed blood and reagent while the mixed blood and reagent resides in the testing chamber.

In some embodiments described herein, a cartridge device may include a blood sample receiver, and a plurality of blood sample pathways in selective fluid communication with the blood sample receiver. Each blood sample pathway may include: a blood measurement chamber to receive a predetermined amount of a blood sample via the blood sample receiver, a reagent mixing chamber for receiving and mixing the predetermined amount of the blood sample with one or more reagents, and a blood coagulation blood testing chamber for receiving from the reagent mixing chamber the blood sample with one or more reagents mixed therewith. Optionally, the blood coagulation blood testing chamber may have a movable probe therein for measuring blood coagulation characteristics.

Various embodiments described herein include a cartridge device for a measuring system for measuring viscoelastic characteristics of a blood sample. The cartridge may include a blood sample receiver; and at least one blood sample pathway in selective fluid communication with the blood sample receiver. The blood sample pathway may include: a blood measurement chamber configured to be filled with a predetermined amount of a blood sample via the blood sample receiver, a reagent mixing chamber for receiving the predetermined amount of the blood sample from the blood measurement chamber and for and mixing the predetermined amount of the blood sample with one or more reagents, and a blood coagulation blood testing chamber for receiving from the reagent mixing chamber the blood sample with one or more reagents mixed therewith, and an overflow chamber in fluid communication with the blood sample pathway so as to collect excess blood from the blood measurement chamber beyond the predetermined amount the blood sample. Optionally, the blood coagulation blood testing chamber may have a movable probe therein for measuring blood coagulation characteristics.

Other embodiments described herein include a measuring system for measuring viscoelastic characteristics of a blood sample. The system may include a control unit housing viscoelastic measurement components. The control unit may define an exterior port. The system may also include at least one disposable cartridge comprising a blood sample input accessible along an exterior of the cartridge and a plurality of blood testing chambers positioned along an interior of the cartridge. Optionally, the control unit is configured to releasably mate with the disposable cartridge when inserted into the exterior port such that the blood sample input of the cartridge remains external to the control unit while the plurality of blood testing chambers are positioned within the control unit.

Some embodiments described herein include a method of using a system for measuring viscoelastic characteristics of a blood sample. The method may include inserting a disposable cartridge into a blood testing control console such that a blood sample input remains externally exposed. The method may also include attaching a blood sample reservoir to the blood sample input. The method may further include providing user input via a user interface of the blood testing control console so as to initiate an automated transport of blood in the blood sample reservoir to a plurality of blood testing chambers within the cartridge for measuring viscoelastic characteristics of the blood in each of the blood testing chambers.

In particular embodiments described herein, a cartridge device for a measuring system for measuring viscoelastic characteristics of a blood sample may include a blood sample receiver structure defining a cavity configured to releasably mate with a blood sample reservoir container. The cartridge device may also include a plurality of blood testing chambers spaced apart from the blood sample receiver structure and each having a movable probe therein for measuring blood coagulation characteristics. All of the blood testing chambers may be in selective fluid communication the blood sample receiver structure.

In some embodiments described herein, a cartridge device for a measuring system for measuring viscoelastic characteristics of a blood sample may include a plurality of blood testing chambers for measuring blood coagulation characteristics. Each of the blood testing chambers may be exposed to atmosphere and may have a sample input port positioned along a sidewall of the blood testing chamber. Optionally, each of the blood testing chambers is in fluid communication with an output port of a respective reagent mixing chamber that is defined in cartridge device at a height below the sample input port of the blood testing chamber.

In various embodiments described herein, a cartridge device for a measuring system for measuring viscoelastic characteristics of a blood sample may include a plurality of reagent mixing chambers for receiving and mixing a predetermined amount of a blood sample with one or more reagent beads. The cartridge device may also include a plurality of retaining elements extending into the reagent mixing chamber so as to maintain a predetermined vertical position of each of the reagent mixing beads within the mixing chamber. The retaining elements of at least one of the reagent mixing chambers may engage multiple reagent mixing beads to maintain the multiple reagent mixing beads spaced apart from one another.

In particular embodiments described herein, a cartridge device for a measuring system for measuring viscoelastic characteristics of a blood sample may include a plurality of reagent mixing chambers for receiving and mixing a predetermined amount of a blood sample with one or more reagent beads. The cartridge device may also include a movable mixing element retained with the reagent mixing chamber. The movable mixing element may comprise a material that is inert relative to the blood sample. The cartridge device may further include a plurality of retaining elements extending into the reagent mixing chamber so as to maintain the reagent mixing beads in positions that are spaced apart from the movable mixing element.

Some embodiments described herein may include a method for measuring coagulation characteristics of a blood sample. The method may include detecting a blood testing cartridge being inserted into a receiver portion of a blood testing control unit. The method may also include prompting a user for input via a user interface of the blood testing control unit to initiate automated transport of blood in the blood sample reservoir to one or more blood testing chambers within the cartridge for measuring viscoelastic characteristics of the blood in each of the blood testing chambers. The method may further include automatically transporting to each of the one or more blood testing chambers within the cartridge a predetermined amount of a blood sample from a blood sample receiver of the blood testing cartridge. Optionally, the method may also include moving a probe in each respective blood testing chamber of the cartridge for measuring blood coagulation characteristics. The method may further include displaying via the user interface measurement results of the blood coagulation characteristics.

Other embodiments described herein include a control console for measuring coagulation characteristics of a blood sample. The control console may include a control unit housing that houses at least one interface element configured to releasably receive a disposable cartridge (which, optionally, may have multiple blood testing chambers therein, and multiple measurement components configured to measure coagulation characteristics of the blood sample within the multiple blood testing chambers of the disposable cartridge). The control console may also include one or more heating elements positioned proximate to the interface element and configured to heat the cartridge to a predetermined, test-related temperature (e.g., 37 degrees C. in some embodiments). The control console may further include one or more temperature sensors positioned proximate to the interface element. The control unit may be configured to transport blood to the multiple blood testing chambers of the disposable cartridge after the temperature sensors indicate the multiple blood testing chambers of the disposable cartridge have reached a predefined temperature.

Some or all of the embodiments described herein may provide one or more of the following advantages. First, some embodiments of the thromboelastometry system are configured to be automated so that user interactions with the system are minimized. As a result, human resources—especially in a point-of-care context like a surgical theater—can be utilized with greater efficiency. The reduction of user interactions can also reduce the chances for manual operator errors, such as measuring inaccuracies, reagent mixing errors, and the like. Accordingly, more accurate thromboelastometry results may be attained in some circumstances.

Second, in some embodiments, the cartridge component includes multiple fluid channels that are each individually controllable so that multiple different assays can be performed from a single supply of a blood sample. For example, each fluid channel includes a dedicated valve and a dedicated vent that are controllable by the analyzer console so that the blood flow and testing of each fluid channel is individually controllable. This feature enables the thromboelastometry system to automatically perform sophisticated assay processes.

Third, in some embodiments, the analyzer console can be configured to perform a number of quality-control operations/confirmations so as to ensure the blood test results are not compromised. For example, the analyzer console can be configured to verify the blood testing cartridge is heated to a target temperature (e.g., about 37° C.) prior to the blood sample being distributed to testing chambers of the cartridge. Because temperature of the blood sample can affect the coagulation characteristics in some circumstances, the accuracy of the thromboelastometry results may be enhanced as a result of such temperature-control operations/confirmations.

Forth, in particular embodiments of the cartridge device, the geometry of the blood flow paths through the fluid channels of the cartridge are configured to reduce the potential for disturbing the blood (e.g., causing bubble formation, etc.), and/or damaging the blood, in a manner that may negatively impact the accuracy of the blood test results.

Fifth, in some embodiments, the blood testing cartridge (and, optionally, the blood collection reservoir) can be equipped with one or more computer-readable components so as to promptly transfer relevant information of the analyzer console for each blood sample testing cycle. For example, each cartridge can be labeled with a barcode, near-field communication tag, and RFID tag, or the like that includes information such as, but not limited to, the types of assays to be performed by the cartridge, the type of reagents container within the cartridge, manufacturer information, an expiration date, or the like. In such embodiments, the analyzer console can include a barcode reader (or a reader for a near-field communication tag, a RFID tag, or the like) that scans the barcode upon insertion of the cartridge into the analyzer console. The analyzer console automatically performs appropriate actions in response to the data read from the barcode. In another example, each blood collection reservoir that is to be used with a corresponding cartridge can be labeled with a barcode, near-field communication tag, and RFID tag, or the like that includes information such as, but not limited to, patient information, clinician information, calibration information, or the like (e.g., which is readable by a corresponding reader device of the analyzer console).

Sixth, each fluid pathway of the cartridge can include a mixing chamber with one or more reagents and a mixing element located therein. In some embodiments, the reagents comprise dissolvable reagent beads. The mixing chambers of the cartridge can be configured to separate the one or more reagent beads from each other and to inhibit the mixing element from direct contact with the reagent beads. Further advantages associated with the thromboelastometry systems provided herein are also envisioned, as will be evident from the following disclosure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A, 1B, 2, and 3 are perspective illustrations depicting the components and use of an example thromboelastometry system, in accordance with some embodiments.

Like reference symbols in the various drawings indicate like elements.

DETAILED DESCRIPTION OF ILLUSTRATIVE EMBODIMENTS

Figure 3:
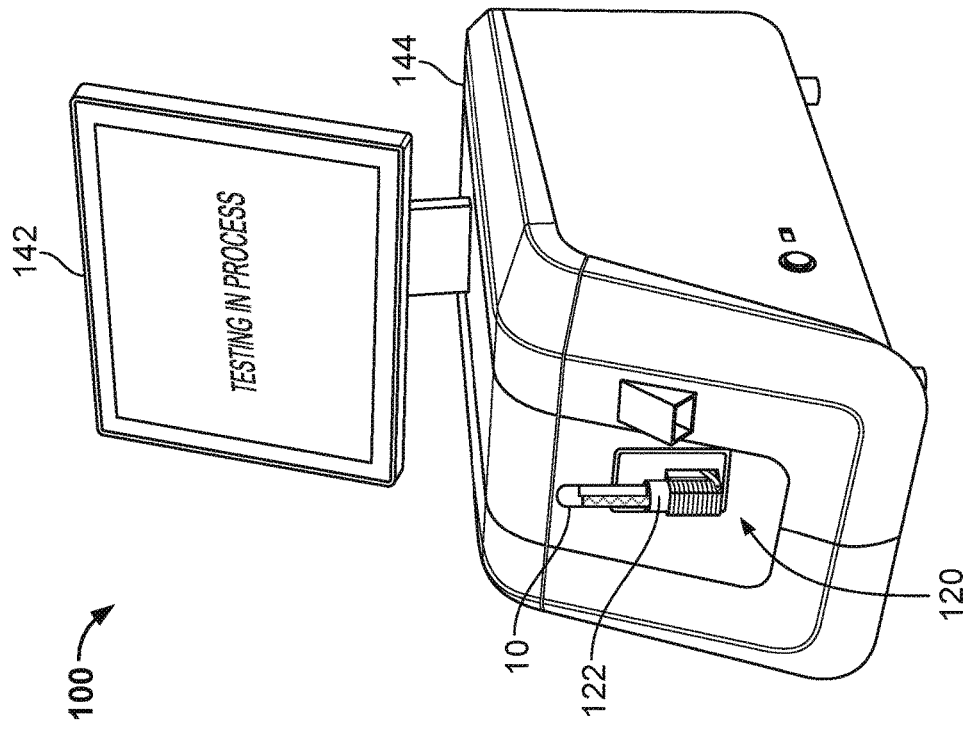

Referring to FIGS. 1A-3, some embodiments of a blood testing system 100 include an analyzer console 140 and one or more cartridges 120 configured to releasably mate with analyzer console 140. In this embodiment, the blood testing system 100 is a thromboelastometry system that is configured to determine a number of blood coagulation characteristics of a blood sample input into the cartridge 120. For example, the cartridge 120 can be configured as a single-use cartridge that includes a blood sample receiver 122 for mating with a blood sample reservoir 10 (e.g., a vacutainer sample tube supplied by Becton, Dickinson & Company of Franklin Lakes, N.J., or another blood reservoir structure). In some cases, an adapter may be used to couple other types of blood sample reservoirs 10 with the cartridge 120 (e.g., tubing may be used through which blood can be injected into the cartridge 120, and the like). The thromboelastometry system 10 can be used as a whole blood coagulation analysis system that is particularly advantageous at a point-of-care site (e.g., in a surgical theater while a patient is undergoing or preparing for surgery, or the like). Additionally, thromboelastometry system 100 can be used as a whole blood coagulation analysis system in a laboratory setting.

The analyzer console 140 includes a user interface 142 (with touchscreen display in this embodiment) and a main chassis 144. The user interface display 142 can be configured to output one or more graphical results 143 from the blood testing assays performed via the cartridge 120 and console 140 (e.g., one or more plots, such as those sometimes refer to as a TEMogram, numeric data or measurements, or a combination thereof). In some embodiments, the user interface display 142 is rigidly attached to the analyzer console 140. In particular embodiments, the user interface display 142 is pivotable and/or is otherwise positionally adjustable in relation to the main chassis 144. A main power switch 148 can be located at a convenient but protected location on the main chassis 144.

In the depicted embodiment, the touchscreen display 142 is configured to receive user input and to display output information to the user. For example, the user can enter information to the thromboelastometry system 100 by making selections of various soft-buttons that may be displayed on the touchscreen display 142 at times during the beginning, middle, and end of the testing process. In some embodiments, other selections such as, but not limited to, soft keyboard entries can be provided via touchscreen display 142. In some embodiments, data entry can be performed additionally or alternatively by voice entry. In other embodiments, the user interface may include other peripheral devices can be included (e.g., a mouse, a keyboard, an additional display device, and the like) as part of the thromboelastometry system 100. In some embodiments, a computer data network (e.g., intranet, internet, LAN, etc.) may be used to allow for remote devices to receive and/or input information from the system 100. For example, in some embodiments one or more remote displays can be utilized via network connections. In the depicted embodiment, the thromboelastometry system 100 also includes an external barcode reader 146. The external barcode reader 146 can facilitate convenient one-dimensional or two-dimensional barcode entry of data such as, but not limited to, blood sample data, user identification, patient identification, normal values, and the like. Alternatively or additionally, the thromboelastometry system 100 can be equipped with a reader configured to read near-field communication tags, RFID tags, or the like.

In the depicted embodiment, the main chassis 144 houses various internal sub-systems (as described further below), includes various electronic connection receptacles (not shown), and includes a cartridge port 150. The various electronic connection receptacles can include network and device connectors such as, but not limited to, one or more USB ports, Ethernet ports (e.g., RJ45), VGA connectors, Sub-D9 connectors (RS232), and the like. Such connection receptacles can be located on the rear of the main chassis 144, or at other convenient locations on the main chassis 144. For example, in some embodiments one or more USB ports may be located on or near the front of the main chassis 144. A USB port, so located, may provide user convenience for recording data onto a memory stick, for example. In some embodiments, the thromboelastometry system 100 is configured to operate using wireless communication modalities such as, but not limited to, Wi-Fi, Bluetooth, NFC, RF, IR, and the like.

Still referring to FIGS. 1A-3, the cartridge port 150 can be located at a readily accessible location on the main chassis 144. In the depicted embodiment, the cartridge port 150 is located on the front of the main chassis 144 so that it is conveniently accessible by a user in a point-of-care site. The cartridge port 150 defines an opening and internal space that is shaped complementarily to the outer dimensions of the single-use cartridge 120. To insert the single-use cartridge 120 into the cartridge port 150, the user can grasp the end of the cartridge 120 that includes the blood sample receiver 122 and slidingly insert the opposite end (leading end) into the cartridge port 150. The sliding insertion can continue until a hard-stop is reached that defines the fully inserted position. In the fully inserted position, a trailing end portion (including the blood sample receiver 122 in this embodiment) of the single-use cartridge 120 remains exterior to the main chassis 144. The portion of the cartridge 120 that is received into the cartridge port 150 can include outer surface features (such as a tapered angle a rear end portion shown in FIG. 1B) that mate with at least one internal interface element inside the console 140 to ensure correct positioning of the cartridge 120. As such, at least the blood sample receiver 122 remains exterior to the main chassis 144 throughout the duration of the blood sample testing. In this configuration, the blood sample receiver 122 serves as a blood sample well that is accessible so that the blood sample reservoir 10 can be inserted into the receiver 122 while the single-use cartridge 120 is mated with the console 140 in the fully inserted position. In some embodiments, the cartridge port 150 and the main chassis 144 are configured so that the exposed portion of the cartridge 120 is protected from inadvertent contact. As described further below, an internal sensor (e.g., a microswitch, an optical sensor, etc.) can detect when the single-use cartridge 120 has been fully inserted into the main chassis 144.

When the analyzer console 140 has detected that the cartridge 120 has been fully inserted, in some embodiments the analyzer console 140 initiates one or more of the following actions. An internal cartridge clamping mechanism that includes positioning pins can be activated to accurately position and releasably retain the single-use cartridge 120 in the fully inserted position. One or more cartridge heating elements can be nalactivated to warm the cartridge 120. The temperature of the cartridge 120 can be monitored. A barcode on the leading end of the cartridge 120 can be read and the barcode data can be stored in memory of the analyzer console 140. One or more blood detection sensors can inspect the cartridge 120 for the presence of blood (which should not be present at this time). The rotational thromboelastometry measuring sub-system can be engaged with the cartridge 120 and, optionally, rotation of the rotary thromboelastometry measuring sub-system can begin (without the presence of blood). The cartridge 120 can be leak tested using vacuum or air pressure delivered by the analyzer console 140. For example, a pressure/vacuum decay test can be performed. In some embodiments, other actions can be additionally or alternatively activated when the analyzer console 140 has detected that the cartridge 120 has been fully inserted. After the completion of such actions, in some embodiments an indication of the results of the actions may be displayed on the touchscreen display 142 (e.g., pass or fail). If the analyzer console 140 determines that the actions were completed successfully, a prompt can be provided on the touchscreen display 142 that informs the user that the thromboelastometry system 100 is ready to receive the blood sample reservoir 10.

Briefly, in some embodiments a user can operate the depicted thromboelastometry system 100 embodiment as follows. First, the user can insert the single-use cartridge 120 into the cartridge port 150 so that the cartridge 120 is placed into the fully inserted position. Completion of that step will automatically initiate a series of operations by the thromboelastometry system 100 as described below. Upon successful completion of such operations, a notification that the blood collection tube 10 can be inserted into the sample well 122 will be displayed on the touchscreen display 142. After the user has mated the blood collection tube 10 into the sample well 122, the user initiates testing by pressing a "start" button (or the like) on the touchscreen display 142. At least the blood measuring, reagent mixing, and thromboelastometry testing is performed automatically by the system 100 thereafter (e.g., without requiring manual intervention from the user in this embodiment). When the testing is completed, the results are displayed on the touchscreen display 142 in the form of qualitative graphical representations and quantitative parameters (e.g., as depicted in FIG. 1A). Also, when the testing is completed, the cartridge 120 can be removed from the console 140 and discarded (e.g., the cartridge 120 in such embodiments is not reusable in that the reagent beads (described below) are no longer present in the cartridge and the measurement chambers contain the clotted blood sample portions).

Alternately, in some embodiments the blood collection tube 10 can be inserted into the sample well 122 of the cartridge 120 prior to insertion of the cartridge 120 into the cartridge port 150. In such circumstances, the blood from the collection tube 10 may not advance to the measurement chambers (described below) of the blood cartridge 120 until after the console 140 acts upon the cartridge 120 (again, as described below). With the blood collection tube 10 being pre-coupled with the cartridge 120, the combination of the blood collection tube 10 and the cartridge 120 can then be inserted into the cartridge port 150.

Figure 4:
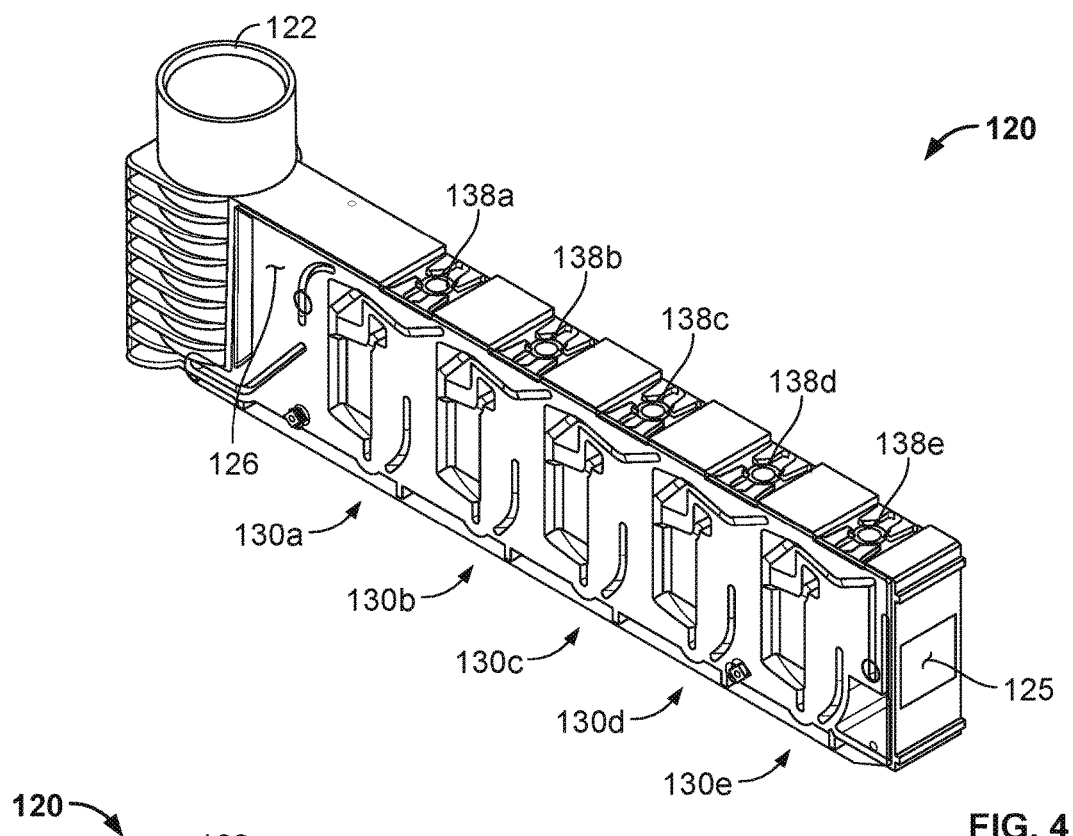
FIG. 4 is a perspective view of the example cartridge component of the thromboelastometry system of FIGS. 1A, 1B, 2, and 3.
Figure 5:
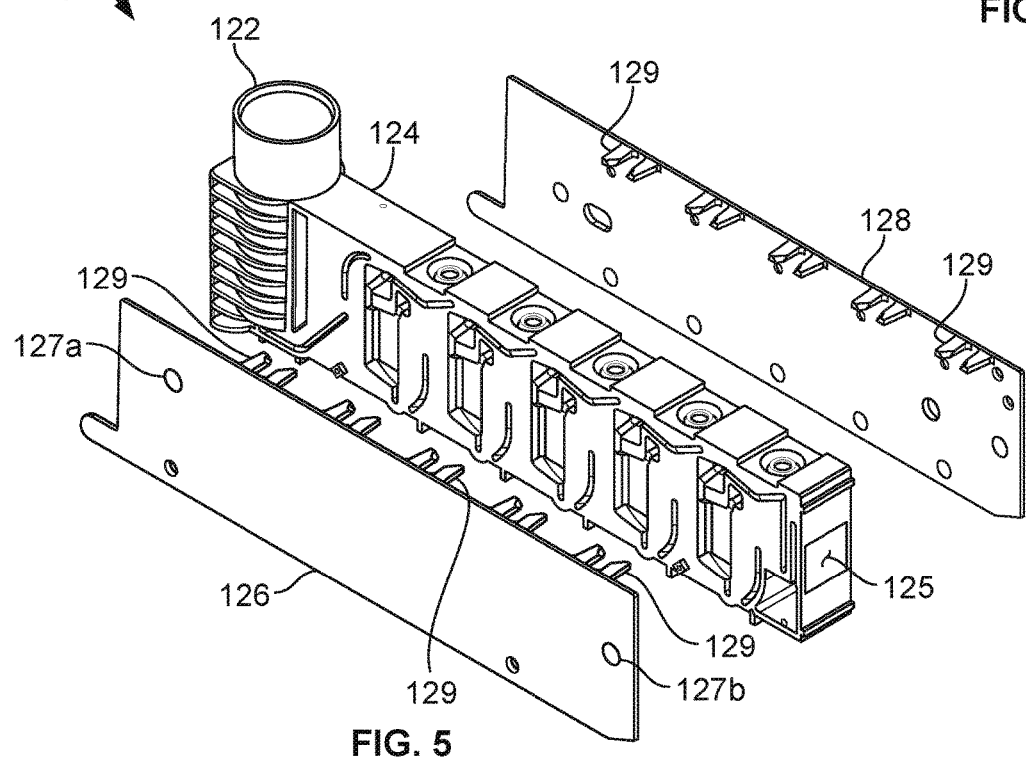
FIG. 5 is an exploded view of the cartridge component of FIG. 4.

Referring now to FIGS. 4 and 5, the depicted embodiment of the single-use cartridge 120 includes a main body 124, a right cover 126, a left cover 128, and five pins 138*a*, 138*b*, 138*c*, 138*d*, and 138*e*. The right cover 126 is affixed to right side of the main body 124, and the left cover 128 is affixed to the left side of the main body 124. As such, the right and left covers 126 and 128 enclose cavities and flow channels of the main body 124 to define blood flow paths as described further below. The aforementioned sample well 122 is part of the main body 124. However, other constructions of the single use cartridge 120 are also envisioned.

In some embodiments, the main body 124, right cover 126, left cover 128, and the pins 138*a*, 138*b*, 138*c*, 138*d*, and 138*e* are made by injection molding. After molding, the right and left covers 126 and 128 can be affixed to the main body 124 using various techniques including, but not limited to, ultrasonic welding, laser welding, solvent bonding, adhesive bonding, UV curable adhesive bonding, and the like. Various polymeric materials can be used to construct the main body 124, right cover 126, left cover 128, and pins 138*a-e*. For example, such polymeric materials can include, but are not limited to acrylic, polycarbonate, polyvinyl chloride (PVC), polyethylene, polypropylene, polymethyl methacrylate, polystyrene, acrylonitrile butadiene styrene (ABS), polyethylene, polypropylene, and the like, and combinations thereof. In some embodiments, the materials are used to construct the main body 124, right cover 126, left cover 128, and pins 138*a-e* comprise an acrylic-based multi-polymer compound. In some embodiments, the main body 124, right cover 126, and left cover 128 are essentially transparent, or at least translucent. Therefore, in FIG. 4, features of the main body 124 are visible even though the right cover 126 is attached thereto.

Figure 7:
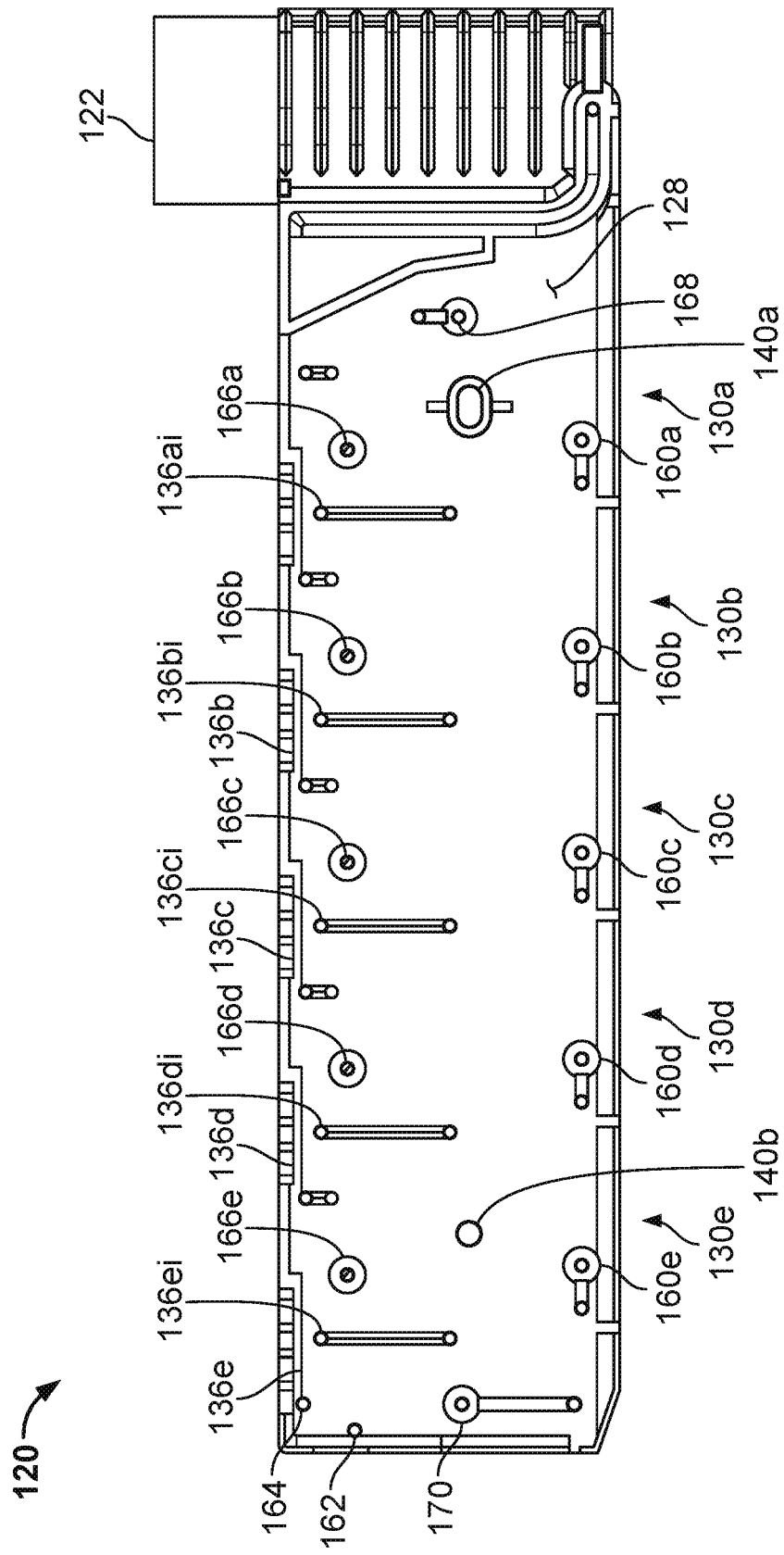
FIG. 7 is a left side view of the cartridge component of FIG. 4.

In some embodiments, overmolding, such as by insert molding or multi-shot molding techniques, may be used to construct some aspects of the main body 124, right cover 126, and/or left cover 128 (i.e., a device component). For example, elastomeric valve elements (as described further below) may be overmolded in the left cover 128. To generate valves by overmolding, a first mask is used to generate a device component without valves. The mask is an inverse of the shape of the device component, the device component including open spaces for later insertion of valves. A polymer is poured into the first mask to form a hard plastic device component. Then a second mask having the inverse of the shape of the device component with the valves is provided. The hardened plastic device component is placed in the mask, and an elastomeric material is injected into the open spaces formed in the device component by the first mask, thereby forming elastomeric valves in the device component. In some embodiments, the device component is the main body 124, right cover 126, and/or left cover 128. Exemplary valves 160*a-e*, 168, and 170 in a left cover 128 formed by overmolding are shown in FIG. 7. In some embodiments, the valves comprise an elastomeric material, deformable upon application of pressure. Deformation of the valves by application of external pressure pushes the elastomeric material into the duct, thereby fluidically sealing the duct to prevent flow of a sample liquid through the duct.

Further, in some embodiments secondary operations may be performed to the cartridge 120. For example, one or more needles 123*a-b* (refer to FIG. 6) for piercing a blood collection tube may be installed within the sample well 122 using secondary operations.

The single-use cartridge 120 also includes the five pins 138*a*, 138*b*, 138*c*, 138*d*, and 138*e*. The pins 138*a-e* are individual component parts (e.g., refer to FIG. 10B) that are retained within openings of the main body 124 (e.g., within testing chambers 136*a-e* (sometimes referred to as "cups") as described further below in connection with FIGS. 8A-10B). Tabs 129, located on the right and left covers 126 and 128, mechanically retain the pins 138*a-e* in the main body 124. However, the pins 138*a-e* are free to move within the confines of the main body 124 to a limited extent. For example, the pins 139*a-e* are free to rotate uninhibitedly within the main body 124 and to translate vertically by few millimeters. This configuration of the pins 138a-e in relation to the other components of the cartridge 120 can be created as follows. Prior to affixing the right and left covers 126 and 128 to the main body 124, the pins 138a-e can be placed within their respective locations in the main body 124 as shown in FIG. 5. With the pins 138a-e positioned in the main body 124, the right and left covers 126 and 128 can then be affixed to the main body 124. With the right and left covers 126 and 128 affixed to the main body and the pins 138a-e positioned in the main body 124, the pins are secured in place vertically by the tabs 129 over the top of the pin 138a-e such that they cannot fall out or be removed from the cup 136a-e without removal of the right and left covers 126 and 128 from the main body 124. The tabs 129 allow free rotational movement of the pin 138a-e, as well as sufficient vertical motion to allow the pin 138a-e to interact with a fluid sample to perform a measurement of viscoelastic characteristics of a fluid sample in the cup 136a-e, e.g., rotational thromboelastometry. In addition, the tabs 129 provide an opening for a shaft 310b to couple with a pin 138b, as shown in FIG. 10C. In one example, the right and left covers 126 and 128 are affixed to the main body 124 and thereafter the pins 138a-e are pushed into the main body 122 past the tabs 129. The tabs 129 of the right and left covers 126 and 128 will block the pins 138a-e from falling out of the main body 122, even if the cartridge 120 is turned upside down. In some embodiments, the pin and tabs are positioned to prevent escape of semi-coagulated fluid sample in the testing chamber from escaping the testing chamber, even if the cartridge 120 is turned upside down.

Figure 2:
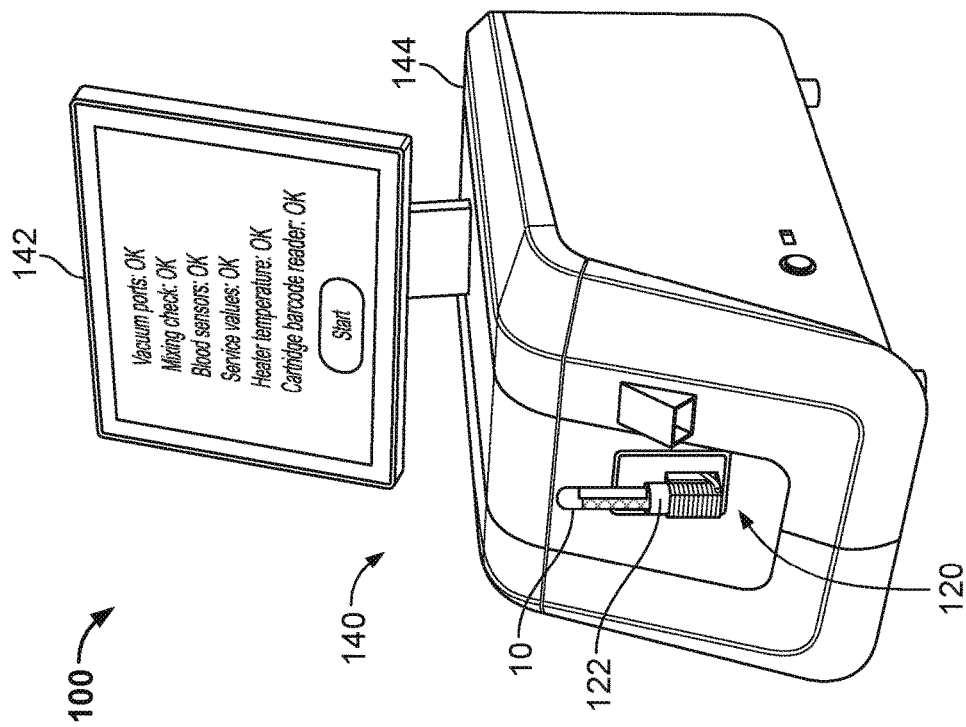

In some embodiments, the main body 124 includes a barcode location 125. The barcode location 125 can be used as a location at which to adhere a barcode label, or to print a barcode. The barcode location 125 is on the leading end of the cartridge 120 (in relation to the direction of insertion of the cartridge 120 into the analyzer console 140 as shown in FIGS. 1-3).

In the depicted embodiment, the right cover 126 includes blood detection locations 127a and 127b. As will be described further below, the blood detection locations 127a and 127b are designated locations on the cartridge 120 at which sensors of the analyzer console 140 interface with the cartridge 120. The sensors inspect for the presence of blood within the cartridge 120 at the blood detection locations 127a and 127b. In some embodiments, the sensors are optical sensors (e.g., infrared sensors) and the blood detection locations 127a and 127b are polished areas that have enhanced transparency and optical clarity. As such, the right cover 126 is configured so that the optical sensors of the analyzer console 140 can readily detect the presence or absence of blood at the blood detection locations 127a and 127b.

Figure 6:
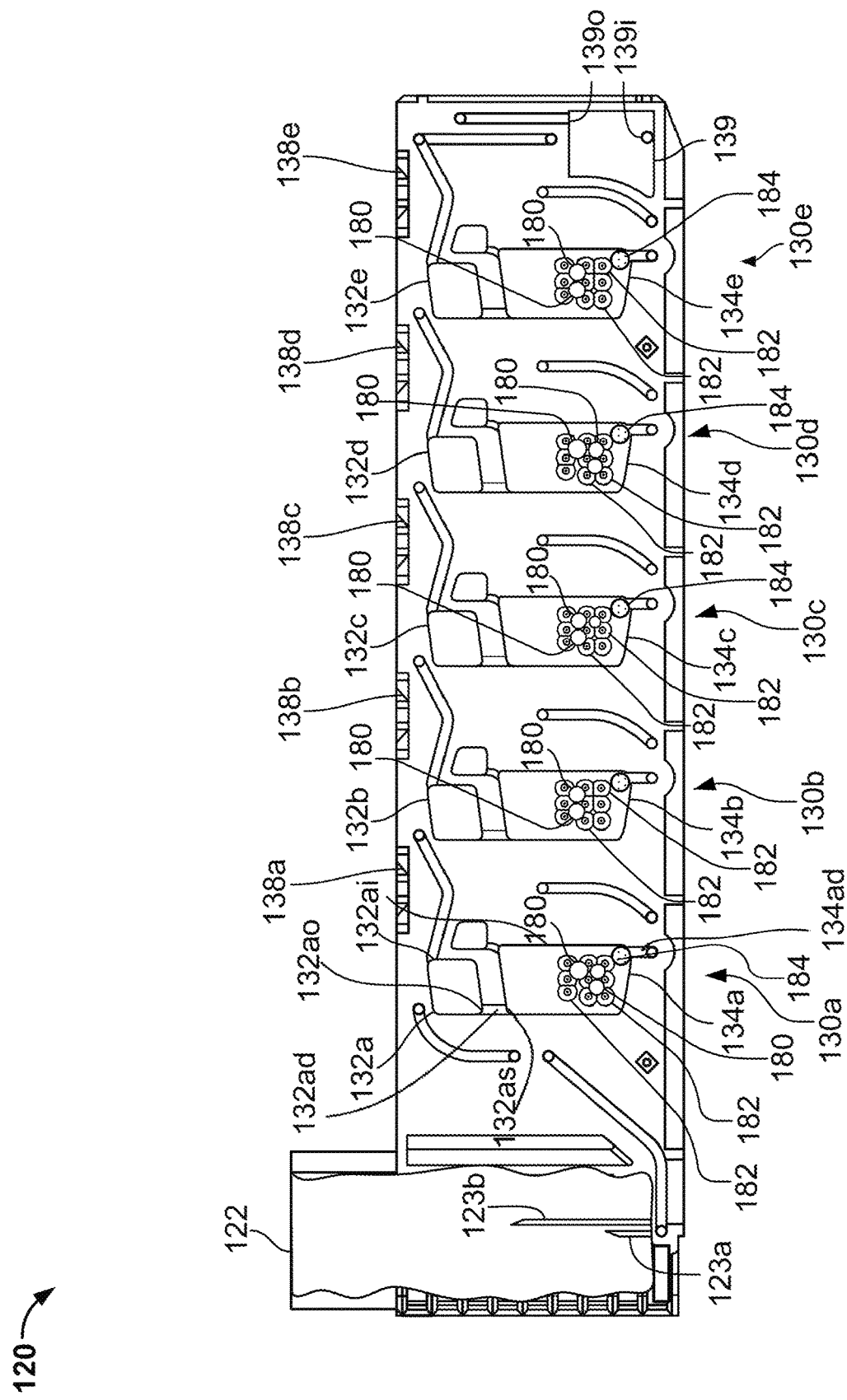
FIG. 6 is a right side partial cutaway view of the cartridge component of FIG. 4.

Referring now to FIGS. 4, 5, and 6, broadly speaking the single-use cartridge 120 is configured to: (i) extract blood from a blood collection tube (e.g., blood collection tube 10 of FIGS. 1-3) and measure a precise volume of the extracted blood, (ii) mix a precise amount of blood with reagents, and (iii) deliver the mixture to multiple cup and pin locations of the cartridge 120 where thromboelastometry testing is performed. These steps will be described in more detail below.

In the depicted embodiment, the single-use cartridge 120 includes five individual blood flow channels 130a, 130b, 130c, 130d, and 130e. Alternately, in some embodiments the cartridge includes a single individual blood flow channel, or two individual blood flow channels, or three individual blood flow channels, or four individual blood flow channels, or six individual blood flow channels, or more than six individual blood flow channels. Each channel 130a-e includes: (i) a measuring chamber, (ii) a mixing chamber containing reagent(s) and a mixing element, and (iii) a blood coagulation testing chamber (e.g., in this embodiment a cup having a movable probe/pin therein). For example, the channel 130a includes a measuring chamber 132a, a mixing chamber 134a, and a testing chamber 136a (refer to the example of the testing chamber being depicted in detail in FIGS. 10A-B). Similarly, the channel 130b includes a measuring chamber 132b, a mixing chamber 134b, and a testing chamber 136b; the channel 130c includes a measuring chamber 132c, a mixing chamber 134c, and a testing chamber 136a; the channel 130d includes a measuring chamber 132d, a mixing chamber 134d, and a testing chamber 136d; and the channel 130e includes a measuring chamber 132e, a mixing chamber 134e, and a testing chamber 136e.

In some embodiments, the sample well 122 includes needles 123a and 123b that are configured to pierce a septum of a blood collection tube when the blood collection tube is inserted into the sample well 122. The needle 123a is in fluid communication with the channels 130a-e, while the needle 123b is a vent that facilitates the ready flow of blood out of the blood collection tube.

In the depicted embodiment, the fluid flow paths from the needle 123a to the channels 130a-e are as follows. The needle 123a is confluent with the measuring chamber 132a. The measuring chamber 132a is confluent with the measuring chamber 132b. The measuring chamber 132b is confluent with the measuring chamber 132c. The measuring chamber 132c is confluent with the measuring chamber 132d. The measuring chamber 132d is confluent with the measuring chamber 132e. Accordingly, blood can flow out of the blood collection tube through the needle 123a to the measuring chamber 132a; from the measuring chamber 132a to the measuring chamber 132b; from the measuring chamber 132b to the measuring chamber 132c; from the measuring chamber 132c to the measuring chamber 132d; and from the measuring chamber 132d to the measuring chamber 132e. The measuring chambers 132a-e may also be referred to as metering chambers 132a-e. Each measuring chamber 132a-e has an inlet port and an outlet port. The inlet ports are located near the top of the measuring chambers 132a-e. For example, measuring chamber inlet port 132ai is located near the top of the measuring chamber 132a. This configuration can be advantageous if the blood contains gaseous bubbles, because such gas may be allowed to escape from the blood as the blood enters the measuring chambers 132a-e. In addition, this configuration may advantageously minimize fluid flow turbulence as the blood flows into the measuring chambers 132a-e, thereby reducing the likelihood of damaging the blood cells.

The outlet ports 134ao-eo for transferring blood from the measuring chambers 132a-e to the mixing chambers 134a-e are located at the bottom of the measuring chambers. For example, measuring chamber outlet port 132ao is located at the bottom of the measuring chamber 132a. In some embodiments, the bottom of the measuring chamber 132a is angled downward towards the outlet port 132ao. In some embodiments, the bottom of the measuring chamber 132a is at an angle of 2°-15° from a plane parallel to the bottom or top of the cartridge 120. In some embodiments, the bottom of the measuring chamber 132a is at an angle of 2°-15° from a plane orthogonal to the direction of force applied to move the blood sample through the outlet port 132ao. In one embodiment, the angles described above are approximately 2°, 3°, 4°, 5°, 6°, 7°, 8°, 9°, 10°, 11°, 12°, 13°, 14°, or 15°. In a preferred embodiment, the angles described above are 5°, although other angles will also be effective. This configuration can help facilitate the complete filling of the measuring chambers 132a-e with blood. It can also minimize transfer of bubbles into the outlet port 132ao as more blood is transferred to the outlet port 132ao before the surface of the volume of blood (which may contain bubbles) contained in the measuring chamber 132a contacts the outlet port 132ao. As such, a precise volume of blood is contained within the measuring chambers 132a-e.

In some embodiments, the top of the measuring chamber 132a is angled to cause air to escape the measuring chamber 132a from a transfer port located at the top of the measuring chamber opposite to the inlet port 132ai. The transfer port is used to transfer air and fluid out of the measuring chamber 132a and into another measuring chamber (e.g., 132b) or into an overflow chamber 139. In this embodiment, the top of the measuring chamber 132a is angled upward from a low point above an inlet port 132ai to a higher point above the transfer port. The angle of the top of the measuring chamber is between 2°-15° when compared to the a plane parallel to the bottom or top of the device, or as compared to a plane orthogonal to the major field of gravitational force applied to the blood sample while in the measuring chamber 132a. In one embodiment, the angle described above is approximately 2°, 3°, 4°, 5°, 6°, 7°, 8°, 9°, 10°, 11°, 12°, 13°, 14°, or 15°. In a preferred embodiment, the angle described above is 5°, although other angles will also be effective. In a device comprising the angled top of the measuring chamber 132a, air and bubbles are transferred out of the measuring chamber 132a before blood, providing a measured blood sample with decreased amount of air that may impact the accuracy of the measurement of the blood, as well as interfere with other downstream applications. In some embodiments, both the top and bottom of the measuring chamber 132a are angled as described above.

From the foregoing description of the fluid flow paths from the needle 123a to the measuring chambers 132a-e, and from the foregoing description of the location of the measuring chamber outlet ports, it should be understood that the measuring chambers 132a-e will be filled with blood in a sequential manner. That is, first measuring chamber 132a will be filled with blood; then blood from measuring chamber 132a will flow to measuring chamber 132b; then measuring chamber 132b will be filled with blood; then blood from measuring chamber 132b will flow to measuring chamber 132c; then measuring chamber 132c will be filled with blood; then blood from measuring chamber 132c will flow to measuring chamber 132d; then measuring chamber 132d will be filled with blood; then blood from measuring chamber 132d will flow to measuring chamber 132e; then measuring chamber 132e will be filled with blood.

After the measuring chamber 132e is filled with blood, then blood from measuring chamber 132e will flow to an overflow chamber 139. The blood flowing from measuring chamber 132e will enter the overflow chamber 139 at an overflow chamber inlet port 139i. As will be described further below, the overflow chamber 139 serves to ensure that the measuring chamber 132e becomes completely full, while preventing blood from exiting the cartridge 120 and flowing into a vacuum source that is used to draw the blood into the measuring chambers 132a-e as described above. The vacuum source is fluidly connected to the overflow chamber 139 at an overflow chamber outlet port 139o. When a negative pressure (with respect to ambient pressure) from the vacuum source is applied at the overflow chamber outlet port 139o, blood from a blood collection tube that is coupled with needle 123a will flow into the cartridge 120 to fill all the measuring chambers 132a-e. Some blood will also exit the measuring chamber 132e and flow towards the overflow chamber 139.

As described further below, various valves and vents are interspersed within the fluid flow paths so that the blood flow can be controlled by the analyzer console according to predefined schemes. In addition, the aforementioned blood detection locations 127a and 127b (refer to FIG. 5) are designated locations on the cartridge 120 at which sensors of the analyzer console 140 interface with the cartridge 120. The sensors inspect for the presence of blood within the cartridge 120 at the blood detection locations 127a and 127b. The blood sensor location 127a is on the fluid flow path between the needle 123a and the measuring chamber 132a. When the analyzer console detects blood at blood sensor location 127a, the analyzer console 140 determines that blood has been drawn into the cartridge 120. The blood sensor location 127b is on the fluid flow path between the measuring chamber 132e and the overflow chamber 139. When the analyzer console detects blood at blood sensor location 127b, the analyzer console 140 determines that blood has been drawn into and filled all the measuring chambers 132a-e. Further, when the analyzer console 140 detects blood at blood sensor location 127b, the analyzer console 140 may cease further application of negative pressure at the overflow chamber outlet port 139o. In other words, by detecting blood at blood sensor location 127b, the analyzer console 140 can determine that the application of vacuum has successfully filled all the measuring chambers 132a-e and that the application of vacuum can be ceased. Optionally, the cartridge 120 may be equipped with a blood temperature sensor at or near the location of blood sensor location 127b so as to verify the blood sample is at a predetermined target temperature.

As described above, each individual channel 130a-e has a measuring chamber 132a-e respectively. In some embodiments, the fluid flow paths within the individual channels 130a-e are as follows. From the measuring chambers 132a-e, the blood can flow to the respective mixing chambers 134a-e. For example, the blood from measuring chamber 132a can flow to the mixing chamber 134a. Similarly, the blood from measuring chamber 132b can flow to the mixing chamber 134b; the blood from measuring chamber 132c can flow to the mixing chamber 134c; the blood from measuring chamber 132d can flow to the mixing chamber 134d; and the blood from measuring chamber 132e can flow to the mixing chamber 134e. From the mixing chambers 132a-e (after completion of the mixing), the blood can flow to the respective testing chambers 136a-e (having a corresponding probe/pin 138a-e therein, refer below to FIGS. 10A-b). For example, the blood from mixing chamber 134a can flow to the testing chamber 136a. Similarly, the blood from mixing chamber 134b can flow to the testing chamber 136b; the blood from mixing chamber 134c can flow to the testing chamber 136c; the blood from mixing chamber 134d can flow to the testing chamber 136d; and the blood from mixing chamber 134e can flow to the testing chamber 136e. Various valves and vents that are controllable by the analyzer console 140 are interspersed within the fluid flow paths of the individual channels 130a-e. Using such valves and vents, the blood flow within the individual channels 130a-e can be controlled by the analyzer console 140 in accordance with predefined schemes.

Referring now to FIGS. 6 and 7, additional features of the cartridge 120 will now be described. In FIG. 6, a side view of particular chambers of the cartridge 120 (measuring chambers 132a-e, reagent mixing chambers 134a-e, and blood coagulation testing chambers 136a-e) is provided. In FIG. 7, a left side view of cartridge 120 and individual channels 130a-e is provided. In this view there is visibility of testing chamber inlet ports 136ai, 136bi, 136ci, 136di, and 136ei for testing chambers 136a-e respectively. The inlet ports 136ai-ei are located near the top of the testing chambers 136a-e, for example, along a side wall of the chamber 136a-e and at a height above the distal head of the pin 138a-e that interacts with the blood sample but below the proximal end of the pin 138a-e (refer to FIG. 10B). This configuration can be advantageous if the blood contains gaseous bubbles, because such gas may be allowed to escape from the blood as the blood enters the cups 136a-e. In viscous solutions, bubbles may be retained at the bottom of the cup 136a-e if the solution enters through the bottom, adversely impacting thromboelastometric measurements by the pin 138a-e in the cup 136a-e. In addition, this configuration may advantageously minimize fluid flow turbulence as the blood flows into the testing chambers 136a-e. Fluid flow turbulence and bubble mixing is also minimized by having a small diameter or blood flow area of the sample inlet port 136bi into the cup 136a-e. Bubbles present in blood from the mixing chamber 134a-e separate from the fluid and remain at the top surface of the blood in the cup 136a-e by using a smaller diameter of a sample inlet port 136bi in combination with the location of the inlet port 136bi along the side wall of the chamber 136a-e. In some embodiments, the diameter of the sample inlet port 136bi is 1 mm. In some embodiments, the diameter of the sample inlet port 136bi is approximately 0.5, 0.6, 0.7, 0.8, 0.9, 1.0, 1.1, 1.2, 1.3, 1.4, or 1.5 mm.

In the depicted embodiment, the cartridge 120 includes two locator pin receptacles 140a and 140b. The locator pin receptacles 140a and 140b are used to mate with locator pins of the analyzer console 140 (as described further below). In this manner, the cartridge 120 can be accurately positioned in relation to the analyzer console 140.

The cartridge 120 also includes a vacuum application port 162. When a source of vacuum is applied at the vacuum application port 162, and when the vents and valves of the cartridge 120 are in the proper configuration, blood can be drawn into the measuring chambers 132a-e as described above, and as described further below.

The cartridge 120 also includes a pressure application port 164. When a source of pressure is applied at the pressure application port 164, and when the vents and valves of the cartridge 120 are in the proper configuration, blood can be forced to flow from the measuring chambers 132a-e into the mixing chambers 134a-e, and subsequently from the mixing chambers 134a-e into the testing chambers 136a-e as described above, and as described further below.

In the depicted embodiment, the cartridge 120 also includes vents 166a, 166b, 166c, 166d, and 166e. Other cartridge embodiments may include fewer or more vents. The vents 166a-e are confluent with the mixing chambers 134a-e respectively. Accordingly, when the vents 166a-e are open to allow airflow therethrough, air from the mixing chambers 134a-e can be readily displaced from the mixing chambers 134a-e as blood flows into the mixing chambers 134a-e. Conversely, when the vents 166a-e are closed to prevent airflow therethrough, blood is inhibited from flowing into the mixing chambers 134a-e because the air within the mixing chambers 134a-e is not allowed to be displaced therefrom. The vents 166a-e can be individually opened and closed by the analyzer console 140 in accordance with predefined schemes as described further below. Accordingly, blood flow into the mixing chambers 134a-e can be controlled as desired.

In the depicted embodiment, the cartridge 120 also includes valves 168, 170, 160a, 160b, 160c, 160d, and 160e. Other cartridge embodiments may include fewer or more valves. The valves 168, 170, and 160a-e are located within fluid flow paths of the cartridge 120. Accordingly, the valves 168, 170, and 160a-e can be actuated (opened or closed) by the analyzer console 140 to allow or to prevent fluid flow through the fluid flow paths in which the valves 168, 170, and 160a-e are respectively located. For example, the valve 168 is located in the fluid flow path between the needle 123a and the measuring chamber 132a. Accordingly, when the valve 168 is open blood can flow from the needle 123a to the measuring chamber 132a, and when the valve 168 is closed blood cannot flow from the needle 123a to the measuring chamber 132a.

The valve 170 is located in the fluid flow path between the measuring chamber 132e and the overflow chamber 139. Accordingly, when the valve 170 is open blood can flow from the measuring chamber 132e to the overflow chamber 139, and when the valve 170 is closed blood cannot flow from the measuring chamber 132e to the overflow chamber 139.

The valves 160a-e are located in the fluid flow paths between the mixing chambers 134a-e and the testing chambers 136a-e respectively. Accordingly, when the valves 160a-e are open blood can flow from the mixing chambers 134a-e to the testing chambers 136a-e respectively, and when the valves 160a-e are closed blood cannot flow from the mixing chambers 134a-e to the testing chambers 136a-e.

As will be described further below, in some embodiments the valves 160a-e can be individually actuated by pins that are translated towards and away from the valves 160a-e. To close the valves 160a-e, the pins can engage with and distend elastomer members of the valves 160a-e so that the elastomer member makes contact with a valve seat of the valves 160a-e. When such pins are retracted away from the elastomer members of the valves 160a-e, the elastomer members will rebound such that the elastomer member is no longer distended and then the valve is opened. The pins can be translated by solenoids in some embodiments.

Other mechanisms to regulate fluid flow in the cartridge 120 may also be present. For example, stop junctions may be placed between the measuring chamber 132a-e and the mixing chamber 134a-e to control the flow of blood from the measuring chamber 132a-e to the mixing chamber 134a-e. In some embodiments, the stop junctions are a barrier that can be opened upon application of a sufficient amount of pressure to the barrier. In some embodiments, the stop junction comprises a narrow area for flow of the sample fluid such that surface tension of the sample fluid prevents flow through the stop junction unless sufficient pressure is applied. Once sufficient pressure is applied, the flow of the sample fluid through the stop junction may continue due to capillary forces.

Referring to FIG. 6 in more detail, some embodiments of the mixing chambers 134a-e contain: (i) one or more dissolvable reagent beads 180, (ii) multiple retaining elements 182, and (iii) a mixing element 184. The one or more reagent beads 180 are disposed within and retained within the confines of the multiple retaining elements 182. The mixing elements 184 are disposed in the bottom portions of the mixing chambers 134a-e, and are free to move horizontally across the bottom portions of the mixing chambers 134a-e. The multiple retaining elements 182 separate the reagent beads 180 from the mixing element 184, and prevent the mixing element 184 from migrating upward away from the bottom portions of the mixing chambers 134a-e. Thus, the multiple retaining elements 182 prevent direct contact of the mixing element 184 with reagent beads 180 in the mixing chambers 134a-e. Preferably, the retaining elements 182 extend into each mixing chamber 134a-e so as to maintain a predetermined vertical position of each of the reagent beads 180 within the mixing chamber (e.g., a vertical position below the height of the blood portion passed into the mixing chamber 134a-e), thereby ensuring that each of the beads 180 will be submerged when the predetermined amount of blood is directed into the respective mixing chamber 134a-e. In an embodiment, the height of the liquid that fills the mixing chamber 134a-e from the measuring chamber 132a-e (i.e., the fill level) is above the retaining elements 182 in the mixing chamber. In some embodiments, the retaining elements 182 are above the height of the fill level of the mixing chamber. In these embodiments, the retaining elements are configured to position the reagent in the path of the fluid such that the reagent is dissolved by the liquid upon entry of the liquid into the mixing chamber. In some embodiments, the flow path is defined as the path the liquid travels to go from one chamber to another, including within the chamber itself after entering from an inlet or duct.

Also, in some embodiments, the multiple retaining elements 182 in each mixing chamber 134a-e maintain each of the reagent beads 180 in the respective mixing chamber 134a-e separate from one another. In such embodiments, each of the reagent beads 180 is not contacted by other beads 180 in the respective mixing chamber 134a-e, is not contacted by the mixing element 184 in the respective mixing chamber 134a-e, and is maintained at a vertical height within the respective mixing chamber 134a-e below the height of the blood portion transported into the respective mixing chamber 134a-e.

The retaining elements 182 may take the form of several unique configurations that result in control over the location of the reagent beads 180. In some embodiments, the retaining elements 182 also prevent contact between different reagent beads 180, contact of reagent beads 180 with the mixing element 184, and/or contact of the reagent beads 180 with other surfaces or components in the mixing chamber 134a-e. In some embodiments, the retaining element 182 is configured to limit movement of the reagent bead 180 within the mixing chamber 134a-e and configured to allow the sample liquid or blood sample to dissolve the reagent bead 180. In some embodiments, the retaining element 182 comprises a barrier. The retaining element 182 can also comprise an inward protrusion or an outward protrusion in the wall of the mixing chamber 134a-e or on the surface of a right cover 126 or left cover 128, or on other surfaces of the device. In some embodiments, the retaining element 182 comprises a channel, a post, or a divot. The retaining element 182 may comprise an array of posts or an array of divots. In some embodiments, the array of posts comprises posts of different diameters to hold reagent beads of different diameters. In some embodiments, the retaining element 182 comprises a compartment or a series of compartments for holding a reagent bead. The retaining element 182 can also be configured to both limit the movement of a reagent bead in the mixing chamber 134a-e, and to allow blood to flow in a way that it contacts and dissolves the reagent bead 180. In some embodiments, the retaining element 182 is configured to allow flow of a blood sample through the mixing chamber 134a-e.

The retaining element 182 can further secure the reagent bead 180 below a predetermined blood sample fill level in the mixing chamber 134a-e. This fill level is determined by the volume of blood provided by the measuring chamber 132a-e, and by the dimensions of the mixing chamber 134a-e and volume of components or reagents within the mixing chamber 134a-e at the time of filling. This fill level can be predetermined based on the above factors. Therefore, the retaining elements 182 are specifically designed to maintain the position of the reagent beads 180 below this predetermined fill level.

Additionally, the retaining elements 182 can limit the movement of a mixing element 184 within the mixing chamber 134a-e. In some embodiments, the resting element 182 used to restrict movement of a mixing element 184 within the mixing chamber 134a-e comprise an array of posts or a compartment that allows a sample fluid or blood sample in the mixing chamber 134a-e to contact the mixing element 184 such that the sample fluid or blood sample is agitated to facilitate dissolving reagents within the mixing chamber 134a-e.

In the depicted embodiment, the one or more dissolvable reagent beads 180 are spherical and are of two different sizes (e.g., about 2 mm diameter and about 3 mm diameter). However, the use of other shapes and/or sizes of reagent beads 180 is also envisioned. In some embodiments, the reagent beads 180 are lyophilized materials, but other forms of materials are also envisioned. The reagent beads 180 can comprise materials such as, but not limited to, $CaCl_2$, ellagic acid/phospholipids, tissue factor, heparinase, polybrene, cytochalasin D, tranexamic acid, and the like, and combinations thereof. The reagent beads 180 are dissolvable in blood. For example, in this particular embodiment, each of the five mixing chambers 134a-e is configured to mix a predetermined volume of blood (as defined by the respective measurement chamber 132a-e) with a different reagent composition (from the one or more reagent beads 180 therein) for purposes of performing five different assays. In this example, the first mixing chamber 134e may include multiple reagent beads 180 the provide $CaCl_2$ and ellagic acid/phospholipids for mixing with the predetermined volume of blood (from the corresponding measuring chamber 132e) so that the first sample portion can be used in a first type of assay. Also in this example, the second mixing chamber 134d may include multiple reagent beads 180 the provide $CaCl_2$, ellagic acid/phospholipids, and heparinase for mixing with the predetermined volume of blood (from the corresponding measuring chamber 132d) so that the second sample portion can be used in a second type of assay. Further, in this example, the third mixing chamber 134c may include multiple reagent beads 180 the provide $CaCl_2$, tissue factor, and polybrene for mixing with the predetermined volume of blood (from the corresponding measuring chamber 132c) so that the third sample portion can be used in a third type of assay. Also in this example, the fourth mixing chamber 134b may include multiple reagent beads 180 the provide $CaCl_2$, tissue factor, polybrene, and cytochalasin D for mixing with the predetermined volume of blood (from the corresponding measuring chamber 132b) so that the fourth sample portion can be used in a fourth type of assay. Lastly, in this example, the fifth mixing chamber 134a may include multiple reagent beads 180 the provide $CaCl_2$, tissue factor, polybrene, and tranexamic acid for mixing with the predetermined volume of blood (from the corresponding measuring chamber 132a) so that the fifth sample portion can be used in a fifth type of assay.

In some embodiments, the reagent bead 180 carrying the CaCl$_2$ reagent is separated from the rest of the beads 180 in the respective mixing chamber 134a-e so as to first allow mixing and then activation/clotting of the a citrated blood sample. Such separation of the reagent bead 180 carrying the CaCl$_2$ reagent may be achieved using the retaining elements 182 (as described above). Alternatively, such separation can be achieved by retaining the reagent bead 180 carrying the CaCl$_2$ reagent in a separate channel or separate mixing chamber that is separated from other beads 180 in the respective chamber 134a-e (such that the blood portion reaches the CaCl$_2$ reagent after the blood portion mixes with other beads 180 within the respective mixing chamber 134a-e). Alternatively, such separation can be achieved by positioning a CaCl$_2$ reagent liquid or a dried-film CaCl$_2$ reagent in a separate channel so that the blood portion reaches the CaCl$_2$ reagent after the blood portion mixes with other beads 180 in the respective mixing chamber 134a-e. Alternatively, the reagent bead 180 carrying the CaCl$_2$ reagent can be coated with an extra layer (and then retained by the retained by the retaining elements 182 as described above) so that the blood portion begins to dissolve the reagent bead 180 carrying the CaCl$_2$ reagent after the blood portion previously mixes with other beads 180 within the respective mixing chamber 134a-e.

Other configurations for providing a reagent to the blood sample may also be used. In some embodiments, a reagent is coated on the wall of a mixing chamber 134a-e. In some embodiments, a reagent is coated on the right cover 126 or the left cover 128. The coated reagent on the right cover 126 or the left cover 128 can be coated in a way that it will at least partially or entirely be contained within the mixing chamber 134a-e. In some embodiments, the reagent is coated so that it remains under the fill level of the mixing chamber 134a-e (the fill level pertaining to the height of blood in the mixing chamber as determined in part by the predetermined volume of blood as measured in the measuring chamber). In some embodiments, the coated reagent is a film layer, i.e., a reagent film. A reagent film is a layer of reagent coated on or near a surface. The reagent film may be liquid or may be dried. A liquid reagent may be retained as a film layer by a dissolvable layer of material placed over the liquid reagent. A liquid reagent layer may also be applied and then dried on the surface. A pre-dried or solid film reagent may also be applied to a surface to form a film layer. In some embodiments, the film layer is in the form of a dissolvable film strip. In some embodiments, certain reagents are preferred to be delivered in a reagent film as opposed to a reagent bead 180. For example, certain reagents that are difficult to lyophilize in a reagent bead 180 may instead be applied on or near a surface in the device as a film layer.

In some embodiments, the coated reagent is in the form of reagent beads 180. Reagent beads may be secured to the wall of a chamber or to a cover using retaining elements 182. The retaining elements 182 may comprise a series of compartments, posts, divots, inward or outward protrusions, or an array of any of the above. Other shapes or configurations of reagent that can be coated or secured to the cover, a wall of a chamber, or within a fluidic passage between chambers, are also envisioned. In some embodiments, both reagent beads 180 and reagent film are coated on one or more surfaces of the device, e.g., in the mixing chamber 134a-e.

A reagent film may also be provided to dissolve in a blood sample in the mixing chamber 134a-e. The reagent film is dissolvable in blood. The reagent film is adhered to a surface in the mixing chamber 134a-e. In some embodiments, a reagent film is deposited on the walls of the mixing chamber 134a-e. In some embodiments, a reagent film is deposited on the right cover 126 or the left cover 128 at a region that at least partially covers or forms a wall of the mixing chamber 134a-e. The reagent film may be used alone, or in addition to one or more reagent beads 180 placed in the mixing chamber 134a-e. Thus, the use of one or more reagent films in a mixing chamber 134a-e provides additional mechanisms of introducing a reagent into a mixing chamber 134a-e to dissolve in the blood.

In some embodiments, the reagent film comprises a lyophilized material, but other forms of materials are also envisioned. The reagent film can comprise materials such as, but not limited to CaCl$_2$, ellagic acid/phospholipids, tissue factor, heparinase, polybrene, cytochalasin D, tranexamic acid, and the like, and combinations thereof. In one particular example, each of the five mixing chambers 134a-e is configured to mix a predetermined volume of blood (as defined by the respective measurement chamber 132a-e) with a different reagent composition (from one or more reagent beads 180 and/or one or more reagent films therein). In this example, the first mixing chamber 134e may include multiple reagent beads 180 and at least one reagent film to provide CaCl$_2$ and ellagic acid/phospholipids for mixing with the predetermined volume of blood (from the corresponding measuring chamber 132e) so that the first sample portion can be used in a first type of assay. Also in this example, the second mixing chamber 134d may include multiple reagent beads 180 and at least one reagent film to provide CaCl$_2$, ellagic acid/phospholipids, and heparinase for mixing with the predetermined volume of blood (from the corresponding measuring chamber 132d) so that the second sample portion can be used in a second type of assay. Further, in this example, the third mixing chamber 134c may include multiple reagent beads 180 and at least one reagent film to provide CaCl$_2$, tissue factor, and polybrene for mixing with the predetermined volume of blood (from the corresponding measuring chamber 132c) so that the third sample portion can be used in a third type of assay. Also in this example, the fourth mixing chamber 134b may include multiple reagent beads 180 and at least one reagent film to provide CaCl$_2$, tissue factor, polybrene, and cytochalasin D for mixing with the predetermined volume of blood (from the corresponding measuring chamber 132b) so that the fourth sample portion can be used in a fourth type of assay. Lastly, in this example, the fifth mixing chamber 134a may include multiple reagent beads 180 and at least one reagent film to provide CaCl$_2$, tissue factor, polybrene, and tranexamic acid for mixing with the predetermined volume of blood (from the corresponding measuring chamber 132a) so that the fifth sample portion can be used in a fifth type of assay.

Further, a reagent film may be deposited on surfaces upstream or downstream from the mixing chamber to mix with the blood sample before or after the mixing chamber. In some embodiments, a reagent film carrying the CaCl$_2$ reagent is placed in a separate channel or separate mixing chamber that is separated from other reagent beads 180 or reagent film in the respective chamber 134a-e (e.g., such that the blood portion reaches the CaCl$_2$ reagent film after the blood portion mixes with other reagent beads 180 and/or reagent films within the respective mixing chamber 134a-e). Alternatively, a CaCl$_2$ reagent film may be deposited in the mixing chamber 134a-e and coated with an extra dissolvable film layer so that the blood portion begins to dissolve the other reagent film carrying the CaCl$_2$ reagent after the blood portion previously mixes with other reagent beads 180 or reagent films within the respective mixing chamber 134*a*-3.

In some embodiments, the reagent bead 180 or reagent film is separated from the rest of the reagent beads 180 or reagent film in the respective mixing chamber 134*a-e* so as to allow mixing with different reagents in a preferred sequence. In one embodiment, such separation of the reagent bead 180 may be achieved using the retaining elements 182 (as described above). Alternatively, such separation can be achieved by retaining the reagent bead 180 or reagent film in a separate channel or separate mixing chamber that is separated from other beads 180 or reagent films in the respective chamber 134*a-e* (such that the blood portion reaches and mixes with the loaded reagents in a preferred sequence). In one embodiment, such separation can be achieved by positioning a reagent liquid, reagent bead 180 or a dried-film reagent in a separate channel so that the blood portion reaches the reagent before or after the blood portion mixes with other reagent beads 180 or reagent films in the respective mixing chamber 134*a-e*. In some embodiments, the reagent bead 180 or reagent film is placed along a duct 134*ad* fluidically connecting the mixing chamber 134*a-e* and the testing chamber 136*a-e*. Alternatively, the reagent bead 180 or reagent film can be coated with an extra layer (and then retained by the retained by the retaining elements 182 as described above) so that the blood portion begins to dissolve the reagent in the reagent bead 180 or reagent film comprising an additional dissolvable layer after the blood portion previously mixes with other reagent beads 180 or reagent films within the respective mixing chamber 134*a-e*.In some embodiments, the coated reagent layer is a dissolvable film layer manufactured from a substrate including a polymeric composition and a reagent. The polymeric composition forms a dissolvable barrier to maintain the coating of the reagent on or near a surface in the device. Upon contact with a blood sample, the polymeric composition dissolves to allow the blood sample to mix with the reagent.

The mixing element 184, comprises a ferromagnetic material including, but not limited to, nickel, cobalt, chromium (IV) oxide, gadolinium, permalloy, and alnico (an aluminum-nickel-cobalt alloy) and the like, and combinations thereof. In the depicted embodiment, the mixing element 184 is spherical and is solid. In other embodiments, the mixing element 184 may have a shape such as, but not limited to, cubical, conical, cylindrical, fan-shaped, elongated, prismatic, and the like, as well as irregular shapes. In some embodiments, the mixing element 184 may include one or more surface features such as protrusions, indentations, or holes, and the like.

As will be described further below, the mixing elements 184 are movable within the mixing chambers 134*a-e* in response to movement of magnets with which the mixing elements 184 magnetically couple. The magnets that the mixing elements 184 magnetically couple with are contained within the analyzer console 140. The movement of the mixing elements 184 encourages the reagent beads 180 to dissolve in the blood contained within the mixing chambers 134*a-e*.

Referring now to FIGS. 8A-8H schematically depict an example fluidic control process 200 that can be used with the thromboelastometry systems provided herein. The process 200 begins with blood contained only within the blood collection tube 10, and ends with blood/reagent mixtures contained in cups 136*a-e* that are configured for rotary thromboelastometry. It should be understood that, in some embodiments, the cartridge 120 (refer to FIGS. 1-7) that is used to implement the fluidic control process 200 is heated (e.g., to about 37° C.) prior to having any blood therein.

Figure 8A:
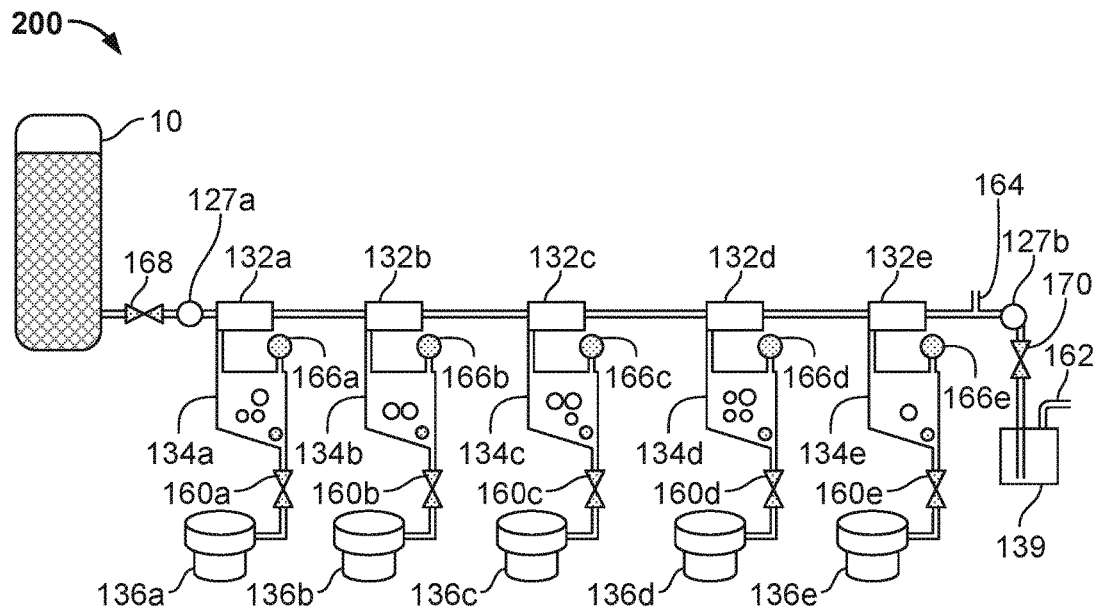
FIG. 8A-8H are a series of schematic diagrams depicting operations of the thromboelastometry system of FIGS. 1A, 1B, 2, and 3, in accordance with some embodiments.

Referring to FIG. 8A, the example fluidic control process 200 includes the blood collection tube 10, the measuring chambers 132*a-e*, the mixing chambers 134*a-e*, and cups 136*a-e*, the overflow chamber 139, the blood detection locations 127*a* and 127*b*, the vacuum application port 162, the pressure application port 164, the vents 166*a-e*, the valves 168, 170, and 160*a-e*. In the depicted configuration, valve 168 is closed, thereby retaining the blood substantially within the blood collection tube 10.

Figure 8B:
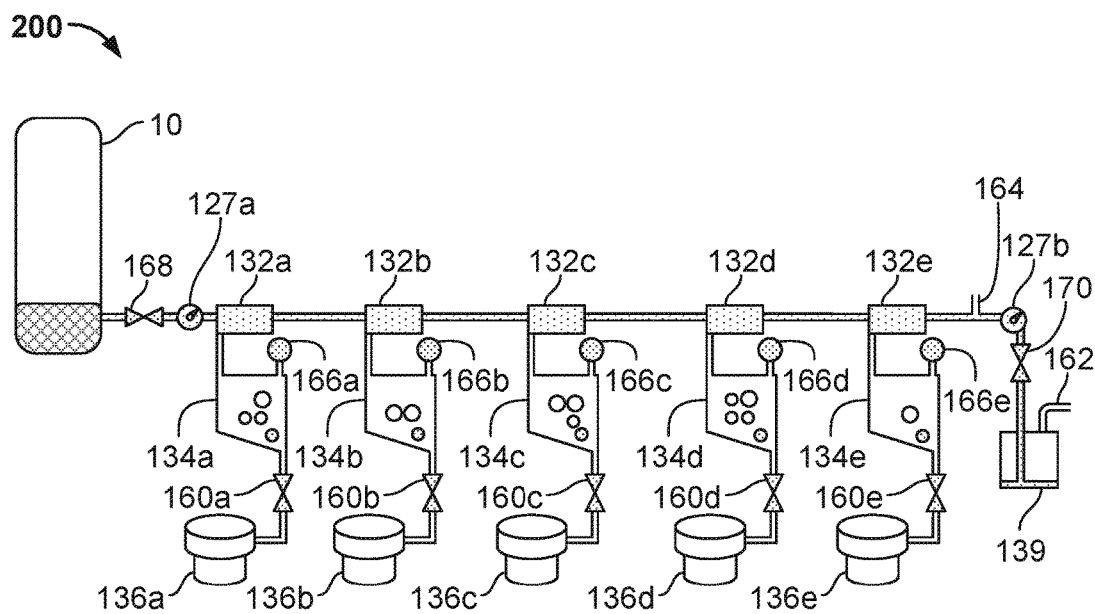

While the example fluidic control process 200 includes five blood flow channels (each comprising a measuring chamber 132*a-e*, a mixing chamber 134*a-e*, and a cup 136*a-e* respectively), it should be understood that having five blood flow channels is not required in all embodiments. For example, in some embodiments only a single blood flow channel is included. Alternately, two blood flow channels are included, or three blood flow channels are included, or four blood flow channels are included, or six blood flow channels are included, or more than six blood flow channels are included. Referring to FIG. 8B, the measuring chambers 132*a-e* are filled with blood, and a small amount of blood is contained within the overflow chamber 139. To arrive at this state, the following changes were made (in comparison to FIG. 8A) and/or the following conditions existed: (i) the valves 168 and 170 were opened, (ii) the valves 160*a-e* were closed, (iii) the vents 166*a-e* were closed, (iv) a negative pressure was applied to the vacuum application port 162, and (v) the pressure application port 164 was unpressurized. Accordingly, the blood flowed: (i) out of the blood collection tube 10, (ii) through the valve 168, (iii) through the blood detection location 127*a*, (iv) into and filling the measuring chamber 132*a*, (v) into and filling the measuring chamber 132*b*, (vi) into and filling the measuring chamber 132*c*, (vii) into and filling the measuring chamber 132*d*, (viii) into and filling the measuring chamber 132*e*, (ix) through blood detection location 127*b*, (x) through valve 170, and (xi) into the overflow chamber 139. When blood was detected in the blood detection location 127*b*, the application of the negative pressure was discontinued—thereby stopping further blood flow.

In some embodiments, the example fluidic control process 200 includes a stop junction 132*as* between one, some, or each of the measuring chambers 132*a-e* and the mixing chambers 134*a-e*. In some embodiments, blood flows through the stop junction 132*as* in the duct 132*ad* connecting the measuring chambers 132*a-e* and the mixing chambers 134*a-e* through application of a positive pressure to the measuring chamber or a negative pressure to the mixing chamber 134*a-e*. Stop junctions provide a mechanism to regulate flow without a connection to an external control device. The application of positive or negative pressure may create a pressure differential on either side of the stop junction, causing the stop junction to open, or drawing blood through the stop junction by overcoming forces due to surface tension. The desired pressure may be applied to cause blood to flow through the stop junction via pressure application port 164 and/or through opening an air pressure vent 166*a-e* to release pressure in the corresponding mixing chamber 134*a-e*.

In some embodiments, the example fluidic control process 200 includes a stop valve in lieu of or in addition to a stop junction between one, some, or each of the measuring chambers 132*a-e* and the mixing chambers 134*a-e*. In some embodiments, the stop valve is a snap acting valve, snapping open upon reaching a set pressure, or a modulating valve that opens in proportion to the pressure differential. Other cartridge embodiments may include pressure-controlled valves in other fluid paths.

In some embodiments, the stop valve may be opened and closed by the same mechanism provided by the valves shown in the reaction system 168, 162, 160*a-e* at FIGS. 8A-8H. In some embodiments, the stop valves may be opened and closed through a mechanism other than pressure application to the blood. In some embodiments, the stop valve is opened upon remote command from a control device connected to the stop valve. In some embodiments, the stop valve can be actuated by the analyzer console 140 to allow or to prevent fluid flow through the fluid path from the measuring chamber 132*a-e* to the mixing chamber 134*a-e*.

Figure 8C:
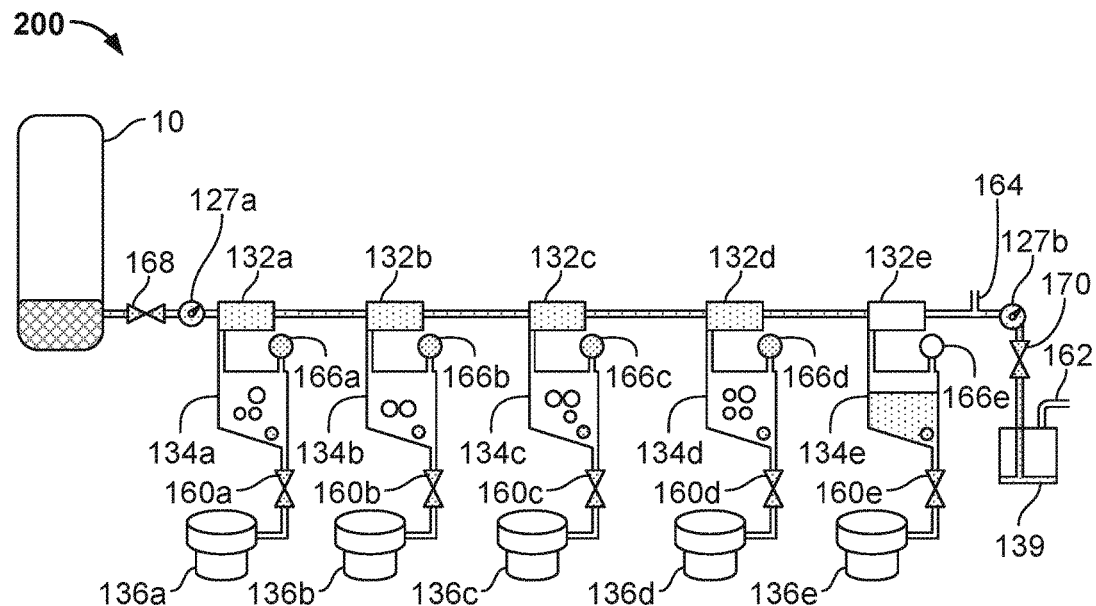

Referring to FIG. 8C, the measuring chambers 132*a-d* are still filled with blood, but the blood from the measuring chamber 132*e* has transferred to the mixing chamber 134*e*. To arrive at this state, the following changes were made (in comparison to FIG. 8B) and/or the following conditions existed: (i) the valves 168 and 170 were closed, (ii) the valves 160*a-e* remained closed, (iii) the vents 166*a-d* remained closed, (iv) the vent 166*e* was opened, and (v) a source of air pressure was applied to the pressure application port 164. Accordingly, the blood flowed: (i) out of the measuring chamber 132*e*, and (ii) into the mixing chamber 134*e*. Because the vents 166*a-d* and the valves 160*a-d* remained closed, the blood in the measuring chambers 132*a-d* did not flow into the mixing chambers 134*a-d*. With blood in the mixing chamber 134*e*, the mixing element in mixing chamber 134*e* can move and agitate the blood to facilitate the dissolving of the reagent beads therein.

In some embodiments, the fluidic control process 200 shown in FIG. 8C includes stop junctions (not shown) between the measuring chamber 132*a-e* and the mixing chamber 134*a-e* to prevent the flow of blood from the measuring chamber to the mixing chamber unless a sufficient pressure differential between the measuring chamber 132*a-e* and the mixing chamber 134*a-e* is applied. In this embodiment, the stop junction prevents leakage of blood from measuring chambers 132*a-d* into mixing chambers 166*a-d* without opening the vents 166*a-d* or applying sufficient pressure to the pressure application port 164 to cause blood to flow through the stop junction. To fill the measuring chamber 132*e* with blood from the mixing chamber 134*e*, the following changes were made (in comparison to FIG. 8B) and/or the following conditions existed: (i) the valves 168 and 170 were closed, (ii) the valves 160*a-e* remain closed, (iii) the vents 166*a-d* remain closed, (iv) the vent 166*e* was opened, and (v) a source of air pressure was applied to the pressure application port 164 to cause blood to flow through the stop junction from the measuring chamber 132*e* into the mixing chamber 134*e*, while the stop junctions between the measuring chambers 132*a-d* and the mixing chambers 134*a-d* prevent flow of blood from the measuring chambers 132*a-d* into the mixing chambers 134*a-d*. With blood in the mixing chamber 134*e*, the mixing element in mixing chamber 134*e* can move and agitate the blood to facilitate the dissolving of the reagent beads therein.

Figure 8D:
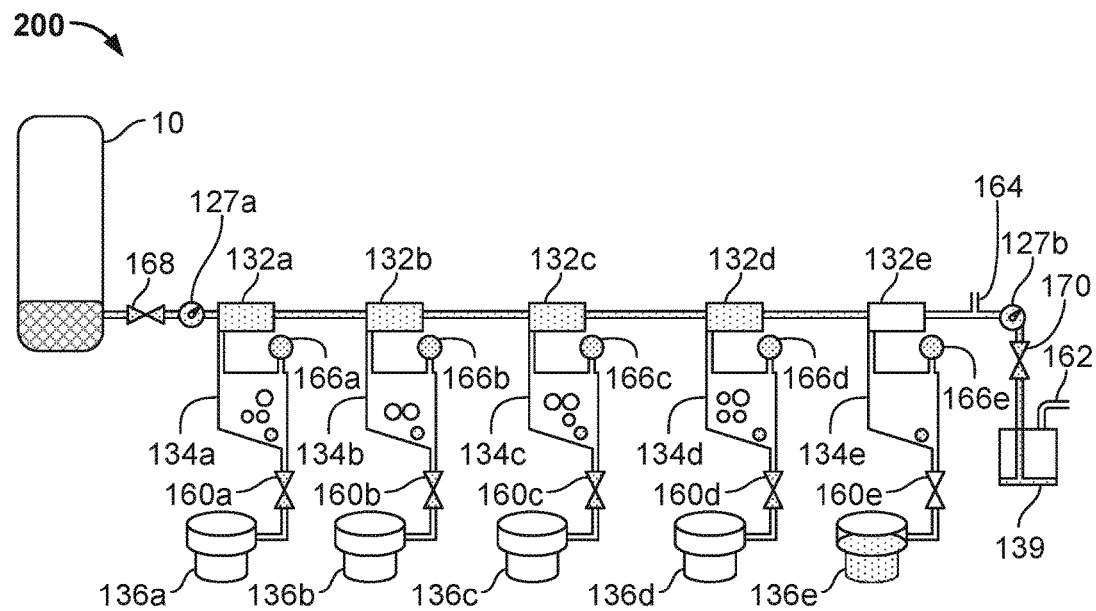

Referring to FIG. 8D, the measuring chambers 132*a-d* are still filled with blood, and the blood/reagent mixture that was in the mixing chamber 134*e* (refer to FIG. 8C) has transferred to the cup 136*e*. To arrive at this state, the following changes were made (in comparison to FIG. 8C) and/or the following conditions existed: (i) the valves 168 and 170 remained closed, (ii) the valve 160*e* was opened, (iii) the valves 160*a-d* remained closed, (iv) the vent 166*e* was closed (v) the vents 166*a-d* remained closed, and (vi) a source of air pressure was applied to the pressure application port 164. Accordingly, the blood/reagent mixture flowed: (i) out of the mixing chamber 134*e*, and (ii) into the cup 136*e*. Because the vents 166*a-d* and the valves 160*a-d* remained closed, the blood did not flow from the measuring chambers 132*a-d* towards the mixing chambers 134*a-d*. With the blood/reagent mixture located in the cup 136*e*, rotary thromboelastometry can begin in the cup 136*e*.

Figure 8E:
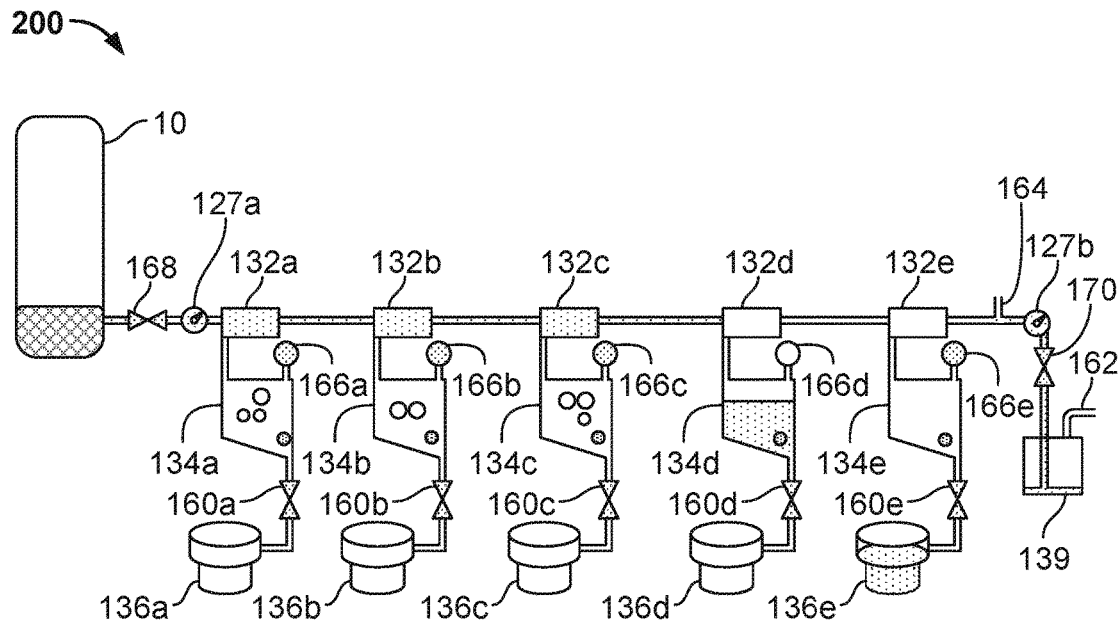

Referring to FIG. 8E, the measuring chambers 132*a-c* are still filled with blood, the cup 136*e* is still filled with blood/reagent mixture, and the blood that was in the measuring chamber 132*d* (refer to FIG. 8D) has transferred to the mixing chamber 134*d*. To arrive at this state, the following changes were made (in comparison to FIG. 8D) and/or the following conditions existed: (i) the valves 168 and 170 remained closed, (ii) the valve 160*e* was closed, (iii) the valves 160*a-d* remained closed, (iv) the vent 166*d* was opened (v) the vents 166*a-c* and 166*e* remained closed, and (vi) a source of air pressure was applied to the pressure application port 164. In embodiments comprising a stop junction between the measuring chamber 132*d* and the mixing chamber 134*d*, the, blood travels through the stop junction by application of pressure differential between the measuring chamber 132*d* and the mixing chamber 134*d*, while the stop junctions between the measuring chambers 132*a-c* and the mixing chambers 134*a-c* prevent flow. Accordingly, the blood flowed: (i) out of the measuring chamber 132*d*, and (ii) into the mixing chamber 134*d*. Because the vents 166*a-c* and because the valves 160*a-c* remained closed, the blood did not flow from the measuring chambers 132*a-c* towards the mixing chambers 134*a-c*. With blood in the mixing chamber 134*d*, the mixing element in mixing chamber 134*d* can agitate the blood to facilitate the dissolving of the reagent beads therein.

Figure 8F:
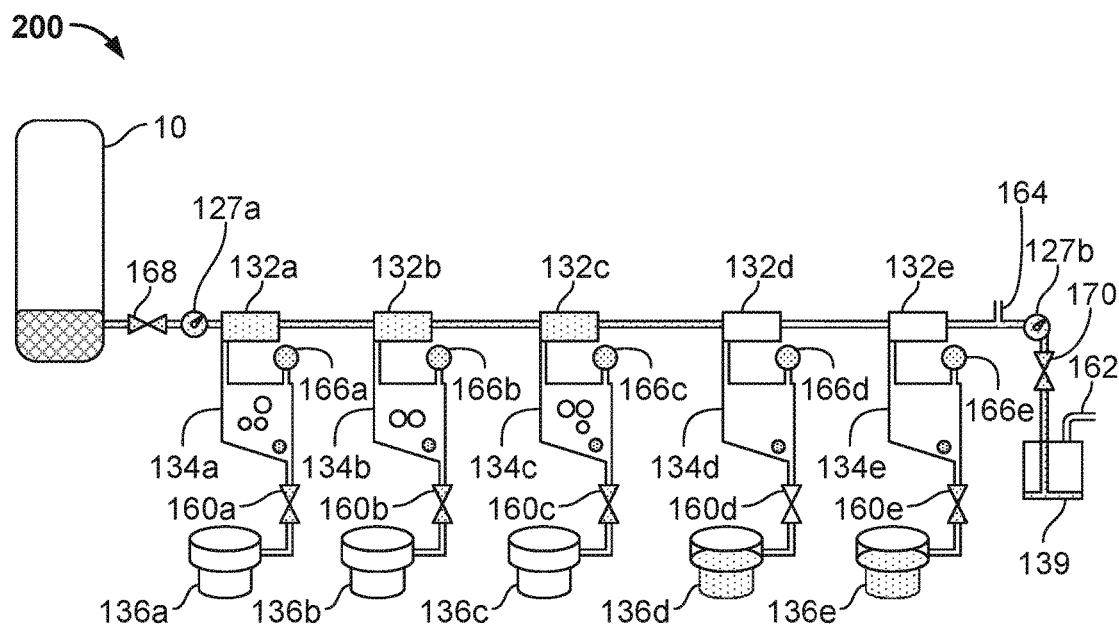

Referring to FIG. 8F, the measuring chambers 132*a-c* are still filled with blood, the cup 136*e* is still filled with blood/reagent mixture, and the blood/reagent mixture that was in the mixing chamber 134*d* (refer to FIG. 8E) has transferred to the cup 136*d*. To arrive at this state, the following changes were made (in comparison to FIG. 8E) and/or the following conditions existed: (i) the valves 168 and 170 remained closed, (ii) the valve 160*d* was opened, (iii) the valves 160*a-c* and 160*e* remained closed, (iv) the vent 166*d* was closed (v) the vents 166*a-c* and 166*e* remained closed, and (vi) a source of air pressure was applied to the pressure application port 164. Accordingly, the blood/reagent mixture flowed: (i) out of the mixing chamber 134*d*, and (ii) into the cup 136*d*. Because the vents 166*a-c* and the valves 160*a-c* remained closed, the blood did not flow from the measuring chambers 132*a-c* towards the mixing chambers 134*a-c*. With the blood/reagent mixture located in the cup 136*d*, rotary thromboelastometry can begin in cup 136*d*.

Figure 8G:
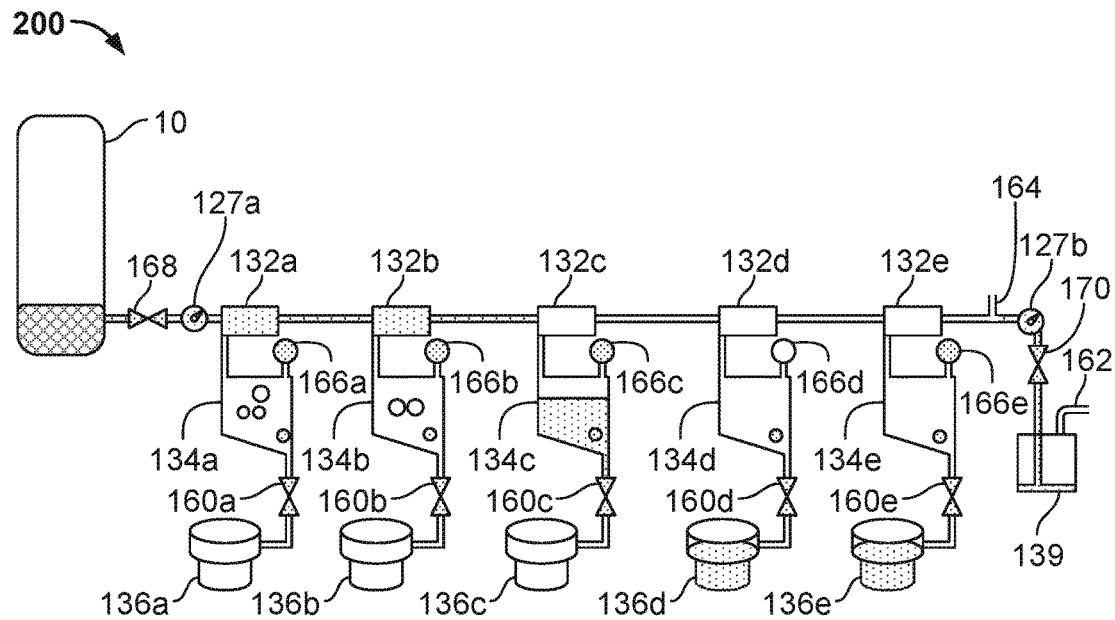

Referring to FIG. 8G, the measuring chambers 132*a-b* are still filled with blood, the cups 136*d-e* are still filled with blood/reagent mixture, and the blood that was in the measuring chamber 132*c* (refer to FIG. 8F) has transferred to the mixing chamber 134*c*. To arrive at this state, the following changes were made (in comparison to FIG. 8F) and/or the following conditions existed: (i) the valves 168 and 170 remained closed, (ii) the valve 160*d* was closed, (iii) the valves 160*a-c* and 160*e* remained closed, (iv) the vent 166*c* was opened (iv) the vents 166*a-b* and 166*d-e* remained closed, and (v) a source of air pressure was applied to the pressure application port 164. In embodiments comprising a stop junction between the measuring chamber 132*c* and the mixing chamber 134c, the, blood travels through the stop junction by application of pressure differential between the measuring chamber 132c and the mixing chamber 134c, while the stop junctions between the measuring chambers 132a-b and the mixing chambers 134a-b prevent flow. Accordingly, the blood flowed: (i) out of the measuring chamber 132c, and (ii) into the mixing chamber 134c. Because the vents 166a-b and because the valves 160a-b remained closed, the blood did not flow from the measuring chambers 132a-b towards the mixing chambers 134a-b. With blood in the mixing chamber 134c, the mixing element in mixing chamber 134c can agitate the blood to facilitate the dissolving of the reagent beads therein.

Figure 8H:
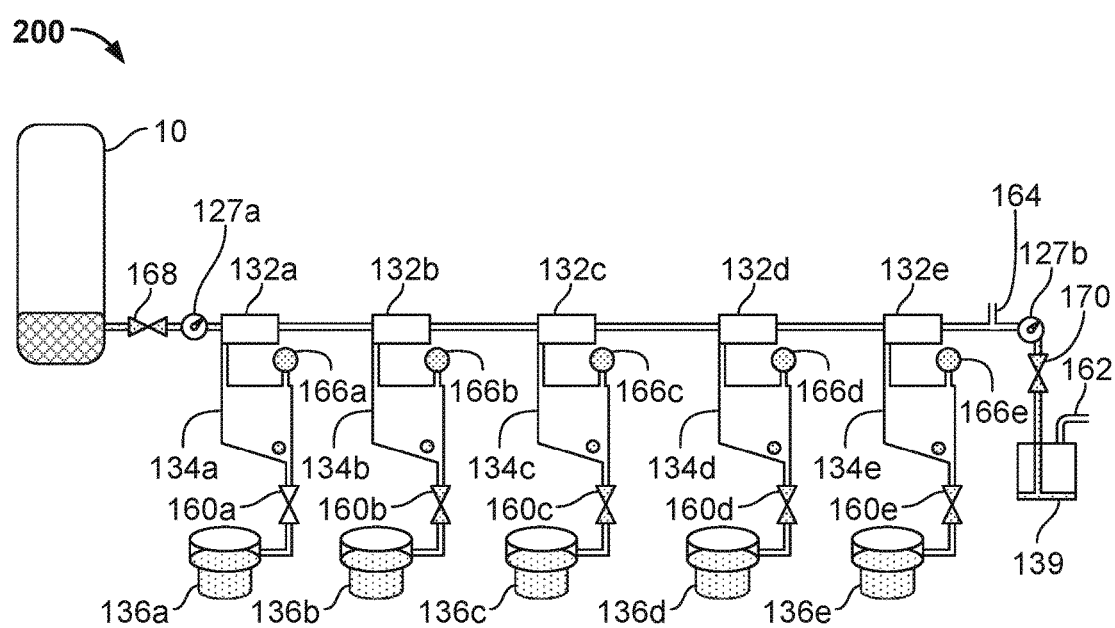

Referring to FIG. 8H, the completion of the process 200 is depicted. That is, the cups 136a-c all contain blood/reagent mixtures and rotary thromboelastometry can be taking place in the cups 136a-e. This state can be attained in accordance with the method of actuating the valves 168, 170, and 160a-e, and the vents 166a-e, in conjunction with applying vacuum to the vacuum application port 162 or pressure to the pressure application port 164 as described above.

Figure 9:
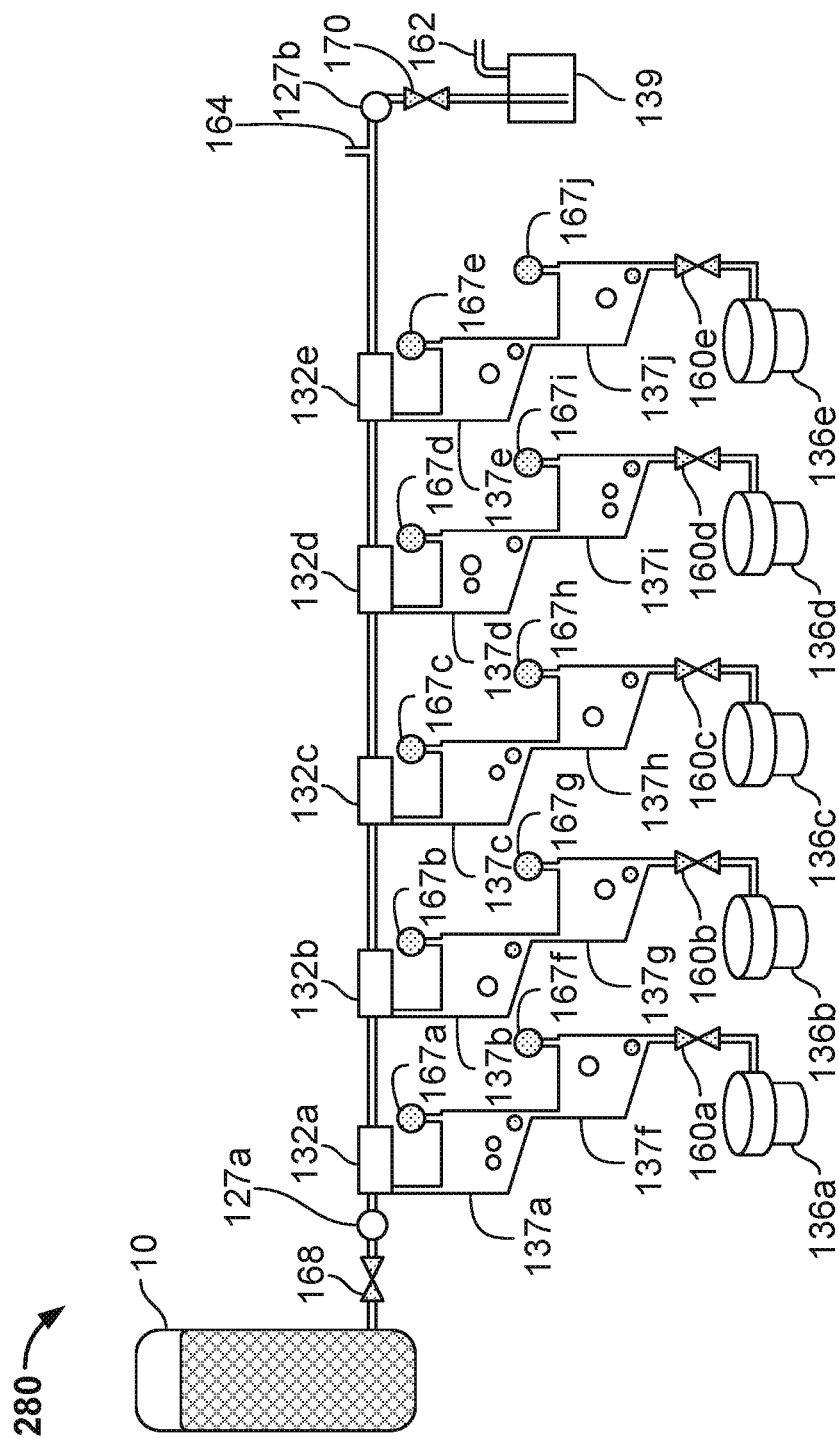
FIG. 9 is a schematic diagram of another example thromboelastometry system, in accordance with some embodiments.

Referring to FIG. 9, in some alternative embodiments, one or more of the individual blood flow channels or paths can include multiple mixing chambers that are arranged in series. For example, the example fluidic control process 280 includes five blood flow channels (similar to the number of channels in the embodiment of FIGS. 8A-H), but each of the channels include two mixing chambers that are arranged in series (rather than a single mixing chamber for each respective mixing chamber like the embodiment of FIGS. 8A-H). That is, mixing chambers 137a and 137f are arranged in series between the measurement chamber 132a and the cup 136a; mixing chambers 137b and 137g are arranged in series between the measurement chamber 132b and the cup 136b; mixing chambers 137c and 137h are arranged in series between the measurement chamber 132c and the cup 136c; mixing chambers 137d and 137i are arranged in series between the measurement chamber 132d and the cup 136d; and mixing chambers 137e and 137j are arranged in series between the measurement chamber 132e and the cup 136e.

In some embodiments, the reagent bead carrying the CaCl$_2$ reagent is separated from the other the reagent beads by locating the CaCl$_2$ reagent in the second of the two mixing chambers that are arranged in series. In that manner, the serial mixing chambers can allow the blood sample to be mixed with reagents and subsequently, at a controlled point in time, activation/clotting of the blood sample can be initiated.

While the example fluidic control process 280 includes five blood flow channels that each include two mixing chambers that are arranged in series, it should be understood that such a configuration is not required in all embodiments. For example, in some embodiments only a single blood flow channel that includes two mixing chambers that are arranged in series is included in a cartridge. Such a single blood flow channel with two mixing chambers may be the only blood flow channel in the cartridge, or may be combined in a cartridge with one or more other blood flow channels that include a single mixing chamber. It should be understood that all combinations and permutations of number of blood flow channels and mixing chambers are included within the scope of this disclosure.

Figure 10A:
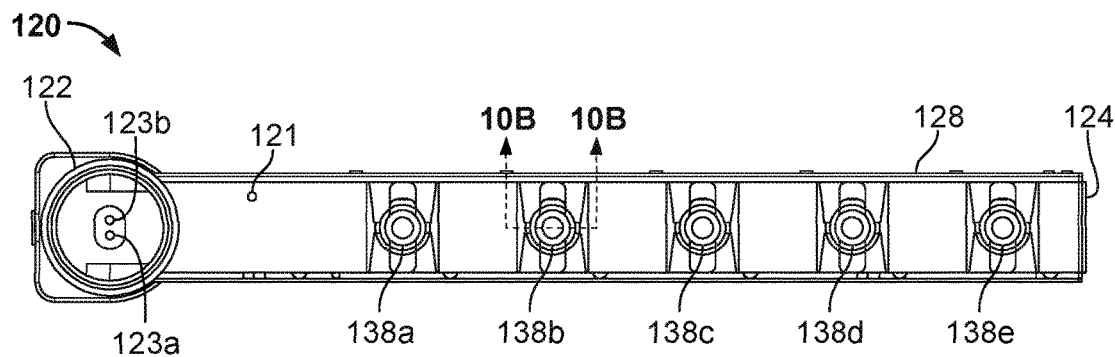
FIG. 10A is a top view of the cartridge component of FIG. 4.
Figure 10B:
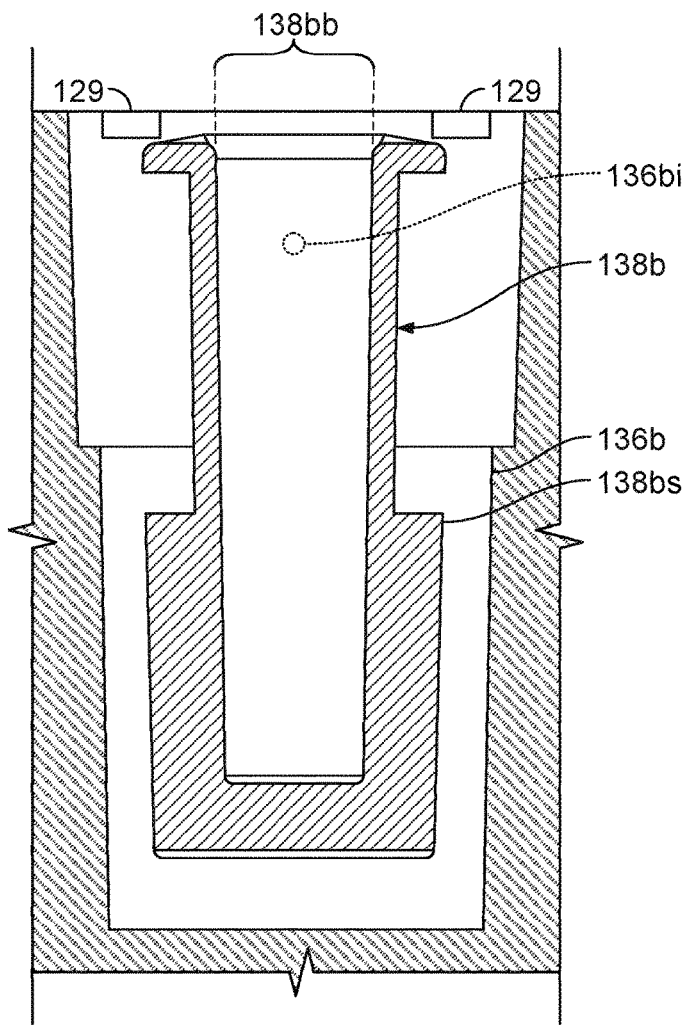
FIG. 10B is a partial cross-sectional view of the cartridge component of FIG. 10A.
Figure 10C:
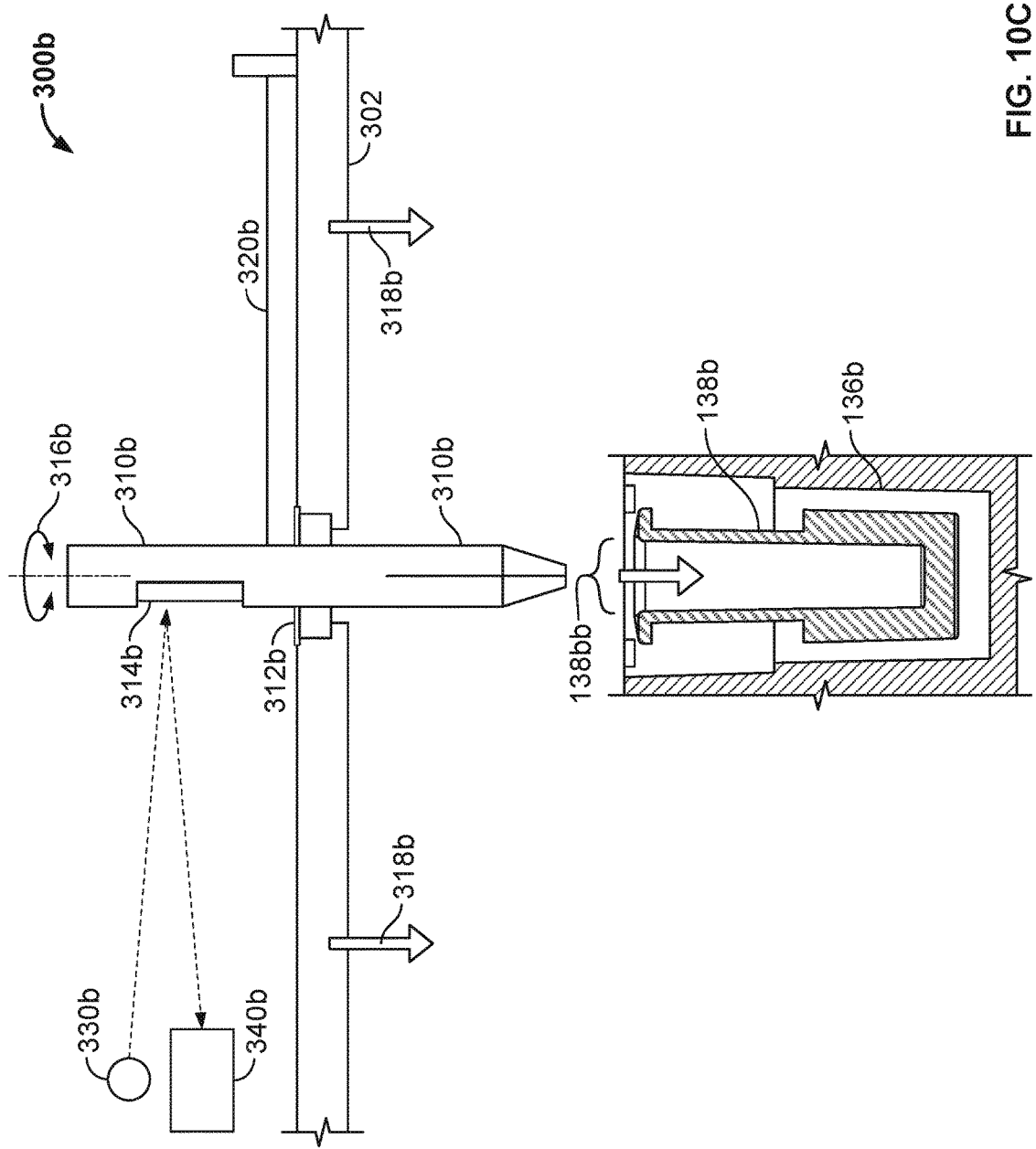
FIG. 10C is a schematic diagram depicting the partial cross-sectional view of the cartridge component of FIG. 10B in conjunction with associated components of an analyzer console of the thromboelastometry system of FIGS. 1A, 1B, 2, and 3.

Turning now to the blood coagulation testing chambers 136a-e in more detail, the chambers 136a-e can be configured to provide viscoelastic testing on the blood sample portion drawn into each chamber. Referring to FIGS. 10A and 10B, the pins 138a-e are located in the cartridge 120. A representative example showing the pin 138b located in the cup 136b illustrates that a clearance space exists between the outer diameter of the pin 138b and the inner diameter of the cup 136b. A blood/reagent mixture will at least partially fill the clearance space when rotary thromboelastometry is being performed therein. The pin 138b has a shoulder 138bs. The clearance space between the outer diameter of the pin 138b and the inner diameter of the cup 136b is less in the areas below the shoulder 138bs than in the areas above the shoulder 138bs. The areas between the outer diameter of the pin 138b and the inner diameter of the cup 136b that are below the shoulder 138bs are the areas that are active in regard to performing rotary thromboelastometry.

The cup 136b and pin 138b are shown in cross-section in FIG. 10B (in accordance with section 10B-10B of FIG. 10A). In addition, a sample inlet port 136bi (located behind pin 138b in the orientation of FIG. 10B) is provided so that the blood/reagent mixture will flow into the cup 136b via the sample inlet port 136bi. In the depicted embodiment, the cup inlet port 136bi is located in a sidewall of cup 136b at a height above the widened distal portion (refer to shoulder 138bs) of the pin 138b but below the proximal end of the pin 138b (refer to end near the entry to the axial bore 138bb of the pin 138b). In this configuration, the blood/reagent mixture will flow into the cup 136b so as to reduce the potential for bubble formation. In addition, locating the cup inlet port 136bi near the top of cup 136b eliminates the effects that the cup inlet port 136bi may otherwise have on the thromboelastometry measurements performed in the cup 136b if the cup inlet port 136bi is located in the active space between the inner diameter of the cup 136b and the outer diameter of the pin 138b below the shoulder 138bs.

In certain devices, bridging or other structure formation between the cup inlet port 136bi (in the interior diameter of the cup 136b) and the outer diameter of the pin 138b (i.e., the probe element) may occur. This may affect the ability of blood to flow into the cup 136a-e, or may cause error in the thromboelastometry measurements taken in the cup 136a-e. In some embodiments, the opening of the inlet port 136bi and the outer diameter of the pin 138b are at least a minimum clearance distance apart that prevents stable bridging of the blood sample or other coagulation structure formation between the pin 138b and the cup inlet port 136bi. At the minimum clearance distance, bridging between the sample inlet port and the pin may still occur upon filling the testing chamber, however, the bridge will not be stable enough to persist during measurement. Typically, a bridge will form around a bubble, which will be instable if the diameter is equal to or greater than the minimum clearance distance. In some embodiments, a stable bridge is one that lasts longer than 1 second, 2 seconds, 3 seconds, 4 seconds, or 5 seconds. In some embodiments, the minimum clearance distance is at least 1.5 mm. In some embodiments, the minimum clearance distance is at least 1.5 mm, 2 mm, 2.5 mm, or 3 mm. In the depicted embodiment in FIG. 10B, the cup inlet port 136bi is located in a sidewall of cup 136b at a height above the widened distal portion (refer to shoulder 138bs) of the pin 138b but below the proximal end of the pin 138b (refer to end near the entry to the axial bore 138bb of the pin 138b), and the inlet port 136bi is at least 1.5 mm from the pin 138b. In other words, the geometry of the pin can allow for this additional clearance since the pin has a narrower portion at the location at which the bridging might occur, thereby allowing for a greater clearance between the pin and the cup to prevent stable bridging.

In the depicted embodiment, the top of the cartridge 124 includes a vent 121. The vent 121 is in fluid communication with the needle 123b. Therefore, when air for venting a blood sample tube located in sample well 122 is needed, air is drawn through the vent 121 and channeled into the blood sample tube via the needle 123b.

Each of the pins 138a-e includes an axial bore. For example, the pin 138b includes an axial bore 138bb. The axial bore 138bb can be used to engage with a shaft (not shown in FIG. 10B) for performing rotary thromboelastometry.

Referring to FIG. 10C, an example rotary thromboelastometry assembly 300b can engage with the pin 138b to perform rotary thromboelastometry on a blood sample contained in the cup 136b. In this particular embodiment, the example rotary thromboelastometry assembly 300b includes a baseplate 302, a shaft 310b, a bearing 312b, a mirror 314b, a counterforce spring 320b, a light source 330b, and a detector 340b (e.g., a charge-coupled device or the like). The baseplate 302 can be lowered, as represented by arrows 318b, such that a tip portion of the shaft 310b enters the bore 138bb to become releasably coupled with the pin 138b. The bearing 312b is engaged with the baseplate 302 and the shaft 310b to facilitate rotational movement of the shaft 310b in relation to the baseplate 302. The counterforce spring 320b is coupled to the shaft 310b and oscillation of the spring 320b can induce the shaft 310b to oscillate back and forth by about +/−5° as represented by arrow 316b. The mirror 315 is coupled to the shaft 310b. The light source 330b is configured to project light towards the mirror 314b, and light can be reflected from the mirror 315 towards the detector 340b (depending on the rotational orientation of the shaft 310b). Accordingly, the motion of the pin 138b is detected by an optical detection system. It should be understood that other configurations of the rotary thromboelastometry assembly 300b are also envisioned within the scope of this disclosure.

The detected motion data is analyzed by an algorithm running on the analyzer console 140 (refer to FIGS. 1-3) to process and determine the thromboelastometry results. This system facilitates various thromboelastometry parameters such as, but not limited to, clotting time, clot formation time, alpha angle, amplitude, maximum clot firmness, lysis onset time, lysis time, lysis index (%), and maximum lysis (%).

As the blood in the cup 136b begins to coagulate, the motion amplitude of the shaft 310b starts to decrease (as detected by the deflection of the light beam from mirror 315 towards the detector 340b). During coagulation, the blood's fibrin backbone (together with platelets) creates a mechanical elastic linkage between the surfaces of the cup 136b and the pin 138b. A proceeding coagulation process induced by adding one or more of the aforementioned activating factors can thus be observed and quantified. In this way, various deficiencies of a patient's hemostatic status can be revealed and can be interpreted for proper medical intervention. At the end of the test process, the baseplate 302 can rise to uncouple the shaft 310b from the pin 138b.

Figure 11:
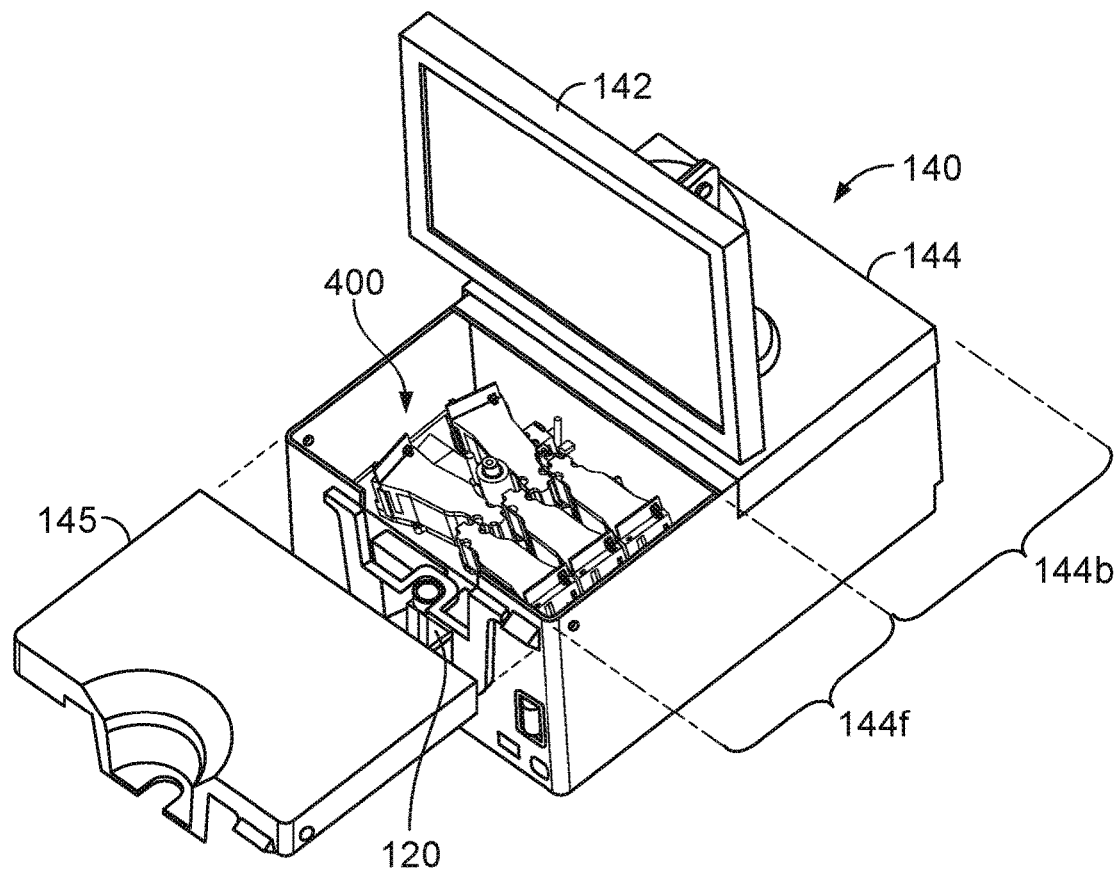
FIG. 11 is an exploded perspective view of a thromboelastometry analyzer console of the thromboelastometry system of FIGS. 1A, 1B, 2, and 3.

Referring to FIG. 11, the main chassis 144 of the analyzer console 140 can include a front portion 144f and a rear portion 144b. In some embodiments, the rear portion 144b houses at least some of the computer and electronic components that are necessary for the operations of the analyzer console 140. For example, the rear portion 144b can house hardware devices and software such as, but not limited to, computer processors, memory devices, an operating system and other executable instructions, power source(s), user interface controls, communication devices, circuit boards, and the like.

In the depicted embodiment, the front portion 144f includes a cover 145 and a sample handler assembly 400. The sample handler assembly 400 defines an interior space in which the cartridge 120 can be received. In some embodiments, the sample handler assembly 400 is a modular sub-assembly of the analyzer console 140, and the sample handler assembly 400 can be readily removed from the analyzer console 140 for service. The sample handler assembly 400 is electrically interconnected with the computer and electronic components that are housed in the rear portion 144b. As such, the analyzer console 140 can perform rotary thromboelastometry on a blood sample located in cartridge 120 and display the results on the touchscreen display 142.

Figure 12:
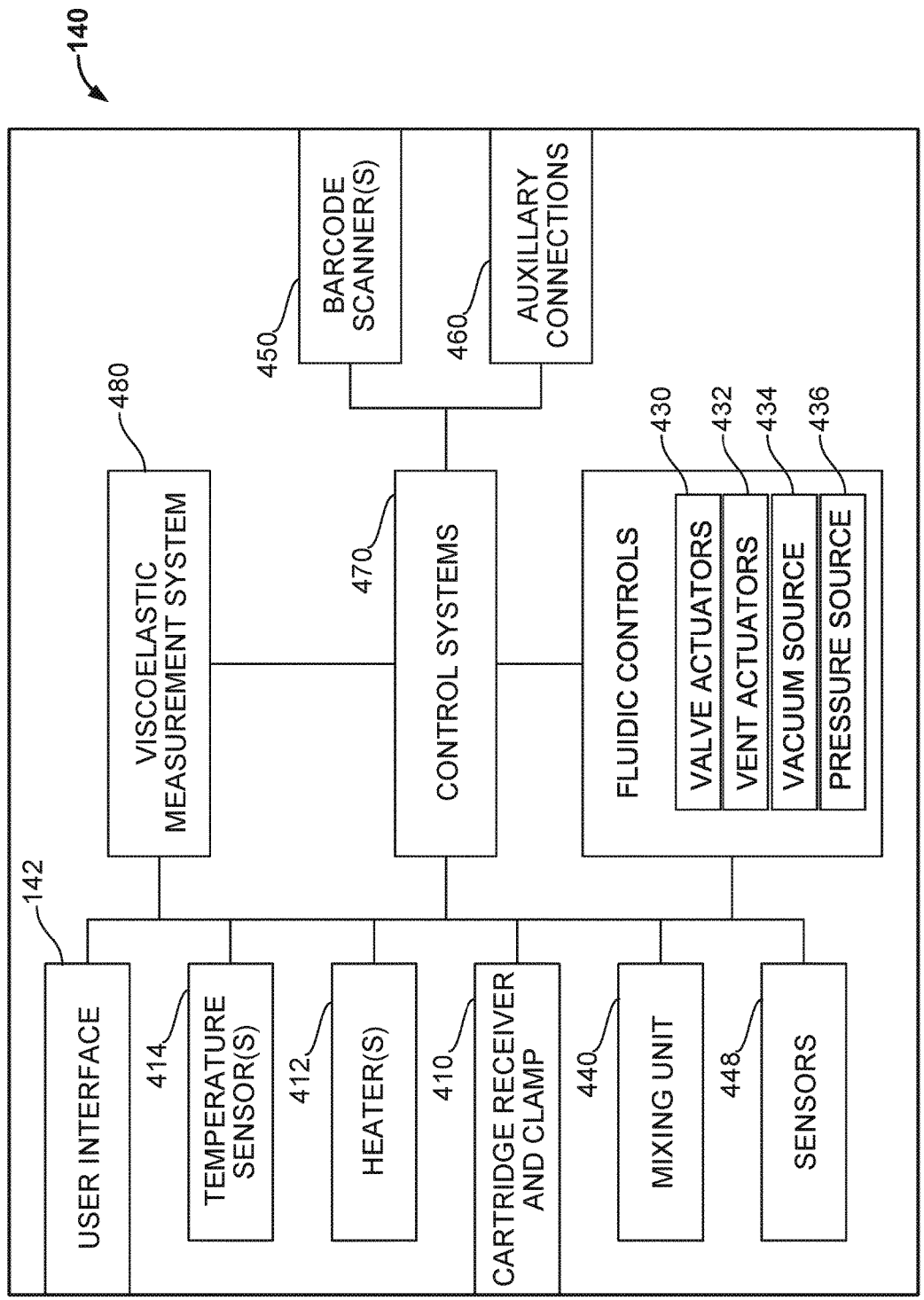
FIG. 12 is a block diagram that schematically depicts subsystems of the thromboelastometry analyzer console of the thromboelastometry system of FIGS. 1A, 1B, 2, and 3.

Referring now to FIGS. 11 and 12, the analyzer console 140 can include a cartridge receiver and clamp 410 and a viscoelastic measurement system 480. A mechanical frame assembly is used to support the cartridge receiver and clamp 410 and the viscoelastic measurement system 480 in orientations such that the cartridge receiver and clamp 410 and the viscoelastic measurement system 480 can function symbiotically.

Portions of the cartridge receiver and clamp 410 and the viscoelastic measurement system 480 are moveable in relation to the mechanical frame assembly (which is stationary in relation to the analyzer console 140). For example, the viscoelastic measurement system 480 can move upward and downward. As will be described further below, the viscoelastic measurement system 480 can move downward to engage with the cartridge 120 (e.g., refer to FIG. 11), and upward to disengage from the cartridge 120. A portion of the cartridge receiver and clamp 410 can move horizontally in relation to the mechanical frame assembly. As will be described further below, a portion of the cartridge receiver and clamp 410 can move horizontally to clamp or unclamp the cartridge 120 within the sample handler assembly 400.

In some embodiments, the cartridge receiver and clamp 410 includes a movable block sub-assembly and a stationary block sub-assembly. A space exists between the movable block sub-assembly and the stationary block sub-assembly in which the cartridge 120 can be received. The movable block sub-assembly can be translated towards or away from the stationary block sub-assembly. Accordingly, the cartridge 120 can be clamped and unclamped between the movable block sub-assembly and the stationary block sub-assembly by virtue of the relative movement therebetween. In some embodiments, the viscoelastic measurement system 480 is mounted to the movable block sub-assembly. Therefore, as the movable block sub-assembly is translated, the viscoelastic measurement system 480 is also translated.

In some embodiments, the moveable block sub-assembly can be translated by an electric motor. In particular embodiments, the motor is a stepper motor. In some embodiments, a gear reducer is coupled to the motor. Using a belt and pulley arrangement for compactness, the motor can be used to drive a lead screw. The threads of the lead screw can be engaged with complementary threads of the movable block such that a rotation of the lead screw results in horizontal translation of the movable block. In some embodiments, end-of-travel detectors (e.g., proximity sensors, optical sensors, micro-switches, and the like) are included to detect when the moveable block sub-assembly has been horizontally translated to the desired end-of-travel positions.

In some embodiments, one or more springs can extend between the movable moveable block sub-assembly and the stationary block sub-assembly. The springs can help facilitate a suitable clamping force between the movable block sub-assembly and the stationary block sub-assembly. In some embodiments, the springs are adjustable.

In some embodiments, portions of the moveable block sub-assembly and the stationary block sub-assembly that make contact with the cartridge 120 comprise a flexible or compressible material so that while the cartridge 120 is clamped it is also protected from damage.

In particular embodiments, the moveable block sub-assembly can include one or more features on the clamping face of the moveable block sub-assembly that serve to position the cartridge 120 in the desired location within the sample handler assembly 400. For example, in some embodiments the moveable block sub-assembly includes two locator pins that can mate with the locator pin receptacles 140*a* and 140*b* of the cartridge 120 (refer to FIG. 7) to accurately position the cartridge 120 in relation to the sample handler assembly 400.

In some embodiments, one or both of the moveable block sub-assembly and the stationary block sub-assembly include heating devices 412 that can warm the cartridge 120 when the cartridge 120 is clamped therebetween. For example, in some embodiments the heaters 412 are electrical resistance heaters that are used to heat at least portions of the cartridge 120. In some embodiments, the heaters 412 are configured to facilitate warming of individual portions of the cartridge 120 independently from other portions of the cartridge 120. For example, one or more of the individual blood flow channels 130*a*, 130*b*, 130*c*, 130*d*, and 130*e* (refer to FIGS. 4-7) can be independently warmed in some such embodiments. Warming may be performed to one or more sides of the cartridge 120. Other types of warming modalities may be used including, but not limited to, IR, ultrasonic, microwave, and the like.

In particular embodiments, one or more temperature sensors 414 are included that can detect the temperature of the cartridge 120 at one or more locations on the cartridge 120. For example, in some embodiments the one or more temperature sensors 414 can be thermocouples, thermistors, infra-red temperature sensors, and the like. Accordingly, the analyzer console 140 can control the heating of the cartridge 120 to a predetermined temperature (e.g., about 37° C.) using the heaters 412 and the temperature sensors 414.

The moveable block sub-assembly can include multiple solenoids that are used to actuate the aforementioned vents and valves of the cartridge 120. For example (referring also to FIG. 7), the valves 168, 170, and 160 *a-e*, can be actuated by valve actuators 430 and the vents 166*a-e* can be actuated by vent actuators 432. In some embodiments, the valve actuators 430 and the vent actuators 432 comprise solenoids. Actuation of the valves 168, 170, and 160 *a-e* by the valve actuators 430 can be accomplished by coupling pins to the valve actuators 430 that are extendable from the moveable block sub-assembly to make contact with and to distend valve elastomer members so that the elastomer members make contact with a valve seat within the cartridge 120. Actuation of the vents 166*a-e* by the vent actuators 432 can be accomplished by coupling pins with resilient tips that are extendable from the moveable block sub-assembly to obstruct the vents 166 *a-e*. Such pins with resilient tips can act as stoppers to substantially prevent airflow through the vents 166*a-e*. In some embodiments, the valve actuators 430 and the vent actuators 432 comprise solenoids that include internal springs that cause the valve actuators 430 and the vent actuators 432 to be normally extended (e.g., when the electrical power is removed from the solenoids). Accordingly, such normally closed solenoids will close the vents and valves of the cartridge 120 as a default configuration.

The sample handler assembly 400 also includes pressure source 436 and vacuum source 434 by which air pressure and vacuum can be applied to the pressure application port 164 and the vacuum application port 162 of cartridge 120 respectively (refer to FIG. 7). For example, the pressure source 436 and vacuum source 434 can make contact with the cartridge 120 and can convey pressure or vacuum to the pressure application port 164 and the vacuum application port 162 when the cartridge 120 is clamped within the cartridge receiver and clamp 410. The pressure source 436 and vacuum source 434 are at least partially made of a resilient material in some embodiments. For example, in some embodiments the pressure source 436 and vacuum source 434 are at least partially made of a resilient material such as, but not limited to, silicone, butyl rubber, nitrile rubber, ethylene propylene rubber, fluoroelastomers, and the like. One or more internally-housed pressure and/or vacuum pumps (not shown) can also be included in the analyzer console 140. Such internally-housed pressure and vacuum pumps can be used to generate the air pressure or vacuum that is applied to the cartridge 120 to induce the transport of blood within the cartridge 120 as described above in reference to FIGS. 8A-8H.

As previously described, the cartridge receiver and clamp 410 also includes the stationary block sub-assembly. In some embodiments, the stationary block sub-assembly does not move in relation to the mechanical frame assembly and in relation to the analyzer console 140 as a whole.

In some embodiments, the analyzer console 140 includes a mixing unit 440. In particular embodiments, the mixing unit 440 includes a motor, a crank and connecting rod assembly, and a magnet shuttle. These components can be used to magnetically couple with the mixing elements of the cartridge 120 and to induce movement of the mixing elements within the mixing chambers 134*a-e*. The movement of the mixing elements encourages the reagent beads to dissolve in the blood contained within the mixing chambers 134*a-e* as described above.

The analyzer console 140 can also include one or more sensors 448. The one or more sensors 448 can be used to detect the presence of blood in particular locations within the cartridge 120, such as blood detection locations 127*a* and 127*b* as described above (refer to FIG. 5). In some embodiments, the sensors 448 are optical sensors, such as IR (infrared) sensors. In some embodiments, the sensors 448 can be used to detect blood in other areas of the cartridge 120, such as, but not limited to, in the cups 136*a-e* (refer to FIGS. 8A-8H).

The sample handler assembly 400 of the analyzer console 140 also includes the viscoelastic measurement system 480. The viscoelastic measurement system 480 includes the baseplate 302 (e.g., refer to FIG. 10C), one or more thromboelastometry assemblies (e.g., thromboelastometry assembly 300*b*), and a linear actuator assembly. The one or more thromboelastometry assemblies can each be affixed to the baseplate 302. In some embodiments, the linear actuator assembly can be coupled to the baseplate 302 and to the cartridge receiver and clamp 410. Accordingly, actuation of the linear actuator assembly can translate the baseplate 302 and the cartridge receiver and clamp 410 towards each other or away from each other. A linear bearing assembly of the linear actuator can guide the baseplate 302 in a linear path, and stabilize the baseplate 302, as the baseplate 302 translates towards or away from the cartridge receiver and clamp 410.

In some embodiments, the linear actuator assembly causes the baseplate 302 to vertically raise or lower in relation to the cartridge receiver and clamp 410 using a motor (e.g., a DC motor or a stepper motor) that rotates a lead screw that has threads that are engaged with a drive nut. The drive nut is coupled to the baseplate 302. In some embodiments, end-of-travel detectors (e.g., proximity sensors, optical sensors, micro-switches, and the like) are included to detect when the baseplate 302 has been vertically translated to the desired end-of-travel positions.

The viscoelastic measurement system 480 includes one of more rotary thromboelastometry assemblies (e.g., rotary thromboelastometry assembly 300b of FIG. 10C) that include a shaft configured to couple with a pin (e.g., the shaft 310b configured to couple with the pin 138b). Because the thromboelastometry assemblies are mounted to the baseplate 302, the shafts are raised or lowered in conjunction with the raising or lowering of the baseplate 302. Accordingly, actuation of the linear actuator assembly causes the shafts to vertically raise or lower in relation to the cartridge receiver and clamp 410, and in relation to a cartridge 120 when a cartridge 120 is clamped within the cartridge receiver and clamp 410. Therefore, from the description herein it can be understood that actuation of the linear actuator assembly can engage and disengage the shafts from the pins of the cartridge 120 (e.g., refer to FIG. 10C that shows baseplate 302 being lowered to engage shaft 310b with pin 138b).

In addition to the aforementioned features of the analyzer console 140, in some embodiments the analyzer console 140 also includes one or more of the following features. The analyzer console 140 can include one or more barcode scanners 450 that, for example, can read a barcode at the barcode location 125 on the leading end of cartridge 120 (refer to FIG. 5). In some embodiments, the analyzer console 140 can include one or more devices to detect the presence of the cartridge 120 in a desired insertion location and/or orientation. For example, in some embodiments one or more micro switches can be used to detect when the cartridge 120 has been inserted in a desired location and orientation within the sample handler assembly 400. In some embodiments, the analyzer console 140 can include one or more auxiliary connections 460. The auxiliary connections 460 can include network and device connectors such as, but not limited to, one or more USB ports, Ethernet ports (e.g., RJ45), VGA connectors, Sub-D9 connectors (RS232), and the like. Such auxiliary connections 460 can be located on the rear of the main chassis 144, or at other convenient locations on the main chassis 144. For example, in some embodiments one or more USB ports may be located on or near the front of the main chassis 144.

The analyzer console 140 also includes a user interface 142 (e.g., with a touchscreen display in this embodiment). In the depicted embodiment, the user interface 142 is configured to receive user input and to display output information to the user. For example, the user can enter information to the analyzer console 140 by making selections of various soft-buttons that may be displayed on the user interface 142 at times during the beginning, middle, and end of the testing process. In some embodiments, other selections such as, but not limited to, soft keyboard entries can be provided via user interface 142. In some embodiments, data entry can be performed additionally or alternatively by voice entry. In some embodiments, the user interface may include other peripheral devices (e.g., a mouse, a keyboard, an additional display device, and the like) as part of the analyzer console 140. In some embodiments, a computer data network (e.g., intranet, internet, LAN, etc.) may be used to allow for remote devices to receive and/or input information from the system 100. For example, in some embodiments one or more remote displays can be utilized via auxiliary connections 460. In the depicted embodiment, the user interface 142 also includes an external barcode reader 146 (refer to FIG. 1A). Alternatively or additionally, the user interface 142 of the analyzer console 140 can be equipped with a reader configured to read near-field communication tags, RFID tags, or the like. The analyzer console 140 can also include one or more control systems 470 that can execute instructions embodied in a computer program. The control systems 470 can include, by way of example, both general and special purpose microprocessors, and any one or more processors of any kind of digital computer. In some embodiments, the control systems 470 includes one or more such processors, memory, storage devices, interfaces, and other types of electronic sub-systems and components. Such components may be mounted on a common motherboard or in other manners as appropriate. The control systems 470 can process instructions for execution within the analyzer console 140, including instructions stored in the memory or on the storage device. In some implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The storage devices are capable of providing mass storage for the control systems 470. In some implementations, the storage device may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above in reference to FIGS. 8A-8H. The computer program product can also be tangibly embodied in a computer- or machine-readable medium, such as the memory, the storage device, or memory on the processor(s).

Figure 13:
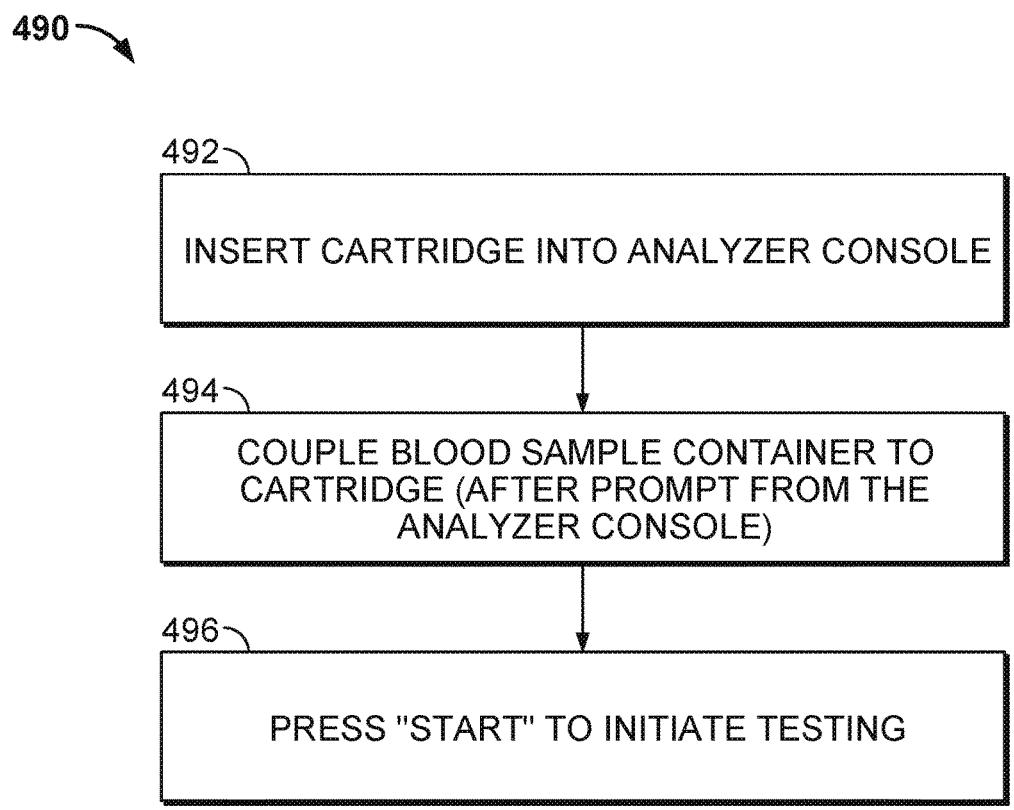
FIG. 13 is a flowchart of a method of using a thromboelastometry system, in accordance with some embodiments.

Referring to FIG. 13, in some implementations a user can interact with the thromboelastometry systems provided herein according to an example process 490. In step 492, the user can insert a cartridge into an analyzer console. In some examples, at least a portion of the cartridge remains exposed while other portions of the cartridge are concealed within the analyzer console. For example, this step is exemplified above in reference to FIG. 1A. In step 494, the user can couple a blood sample container to the cartridge after a prompt is received from the analyzer console. Step 494 can be performed while the cartridge remains inserted in the analyzer console as defined by step 492. At step 496, the user can press a "start" button (or equivalent) to initiate an automated transport of blood in the blood sample reservoir to the blood testing chambers of the cartridge such that the viscoelastic characteristics of the blood can be measured. In some examples, the analyzer console provides an indication that the testing is ready to be initiated, but that indication is not required as part of process 490.

Figure 14A:
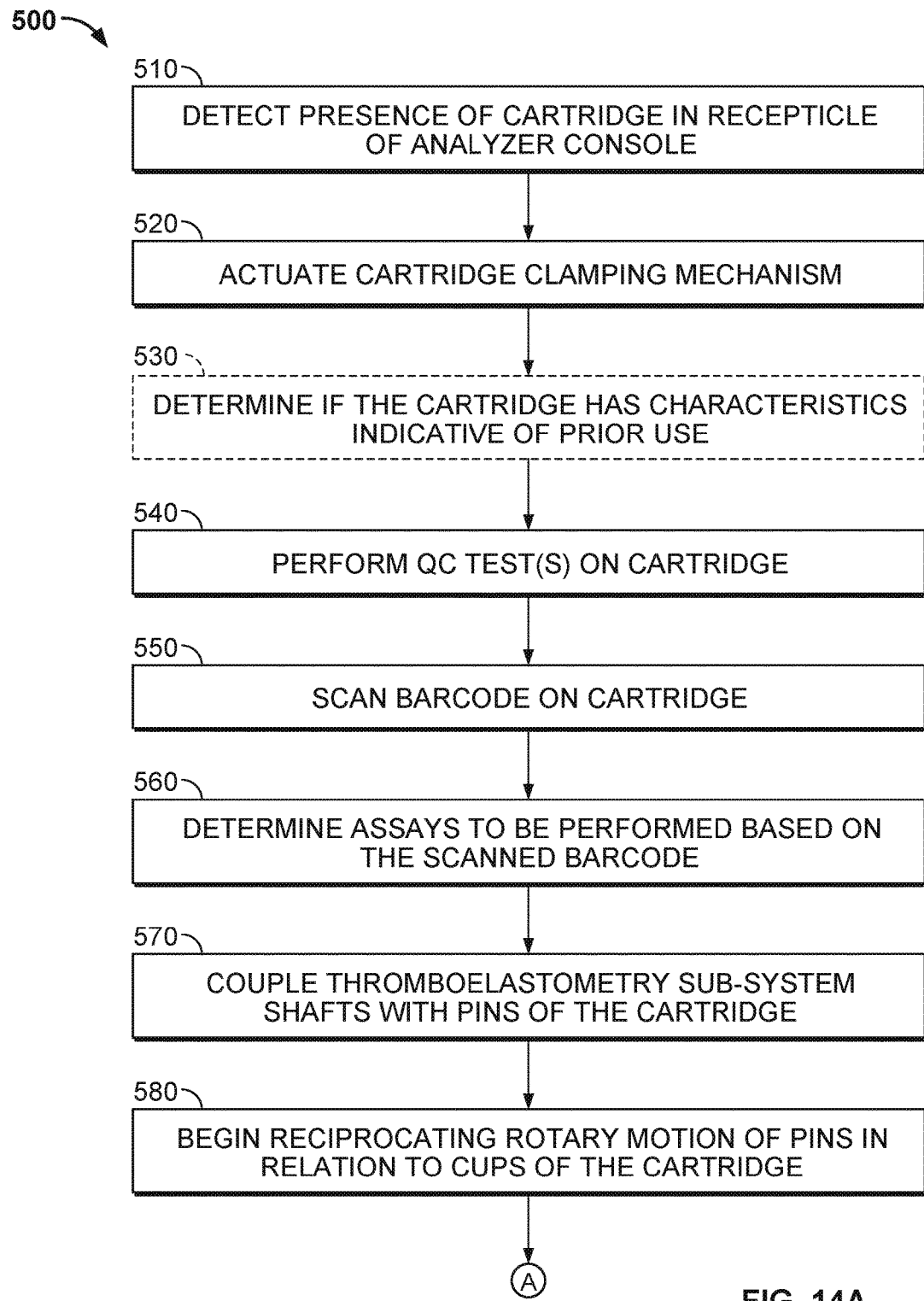
FIGS. 14A and 14B are a flowchart of a method for controlling a thromboelastometry system, in accordance with some embodiments.
Figure 14B:
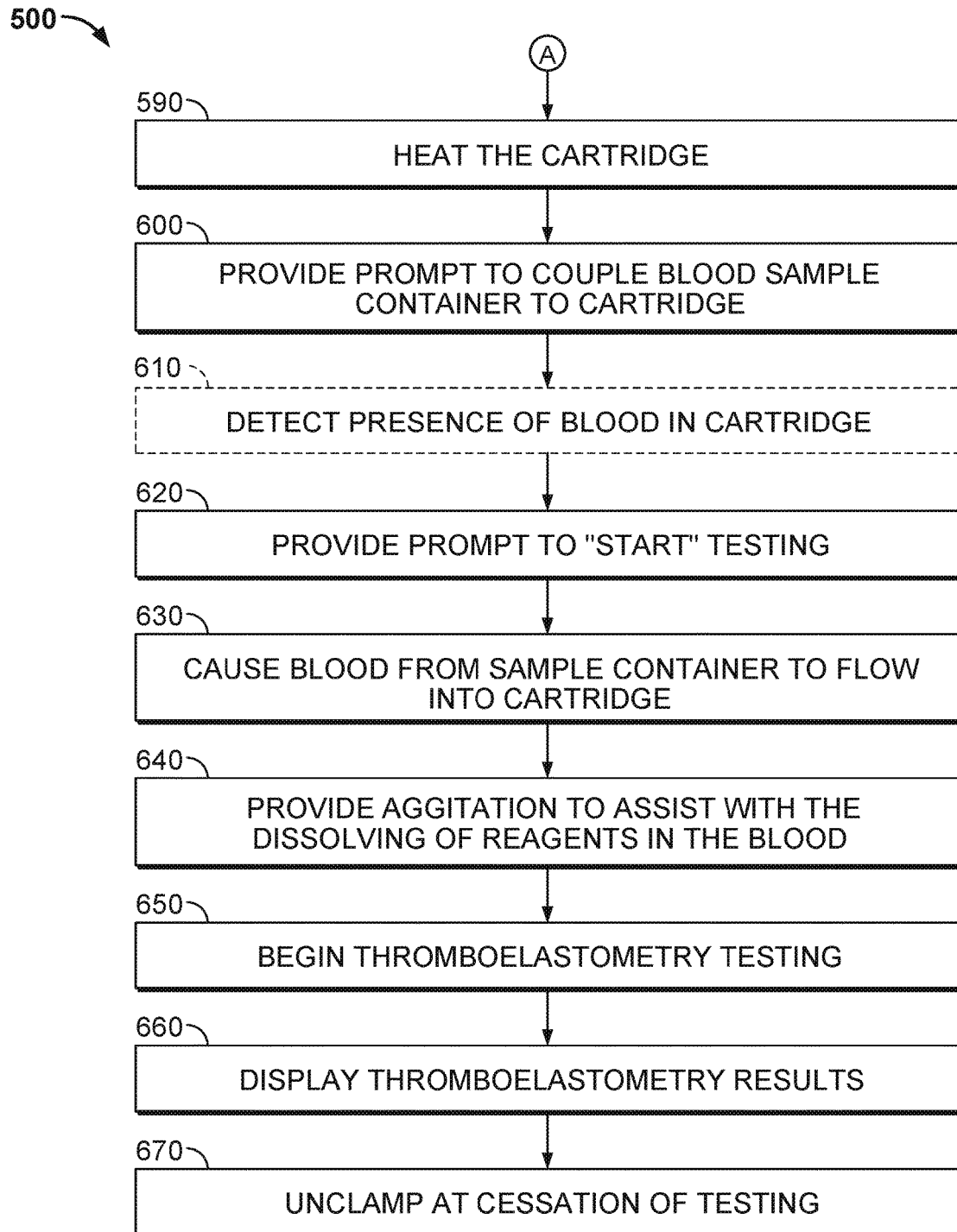

Referring to FIGS. 14A and 14B, in some implementations a thromboelastometry system can perform thromboelastometry according to an example process 500. The individual steps of the process 500 may not necessarily be performed in the order listed. Further, in some implementations some steps of the process 500 may be performed in parallel. The process 500 may be performed by the thromboelastometry systems described above, such as thromboelastometry system 100.

In step 510, the presence of a cartridge is detected in a receptacle of an analyzer console of the thromboelastometry system. For example, the detection may be performed by a micro switch, optical sensor, barcode scanner, and the like, or a combination thereof. Even though the cartridge is detected in the receptacle, at least a portion of the cartridge may be exterior to the analyzer console.

In step 520, the analyzer console actuates a clamping mechanism to clamp the cartridge at least partially in the analyzer console. For example, the cartridge receiver and clamp 410 as described above can be activated to clamp the cartridge.

In step 530, the analyzer console can optionally determine if the cartridge has characteristics that indicate the cartridge has been used previously. For example, the analyzer console may use optical sensors to inspect for the presence of blood in the cartridge. In some embodiments, if one or more characteristics that indicate the cartridge has been used previously are detected, the analyzer console may suspend further steps of process 500 and provide a pertinent message via the user interface.

In step 540, the analyzer console can perform one or more QC tests to test the integrity of the cartridge. For example, in some embodiments the cartridge can be tested for leaks such as by performing a pressure/vacuum decay test.

In step 550, the analyzer console scans the cartridge for a barcode. For example, the analyzer console may scan a leading end of the cartridge at which a 1D or 2D barcode may be present.

In step 560, the analyzer console determined the types of thromboelastometry assays to be performed based on the information attained from the scan of the barcode in step 550.

In step 570, the shafts of the thromboelastometry sub-system of the analyzer console are coupled with pins of the cartridge. The pins are located in cups of the cartridge. Accordingly, the coupling of the shafts of the thromboelastometry sub-system to the pins can configure the thromboelastometry system to be capable of performing thromboelastometry on a blood sample contained within the cups of the cartridge. For example, referring to FIG. 10C, the shaft 310b of the thromboelastometry assembly 300b can be lowered towards the cartridge so that the shafts 310b become friction-fit and releasably coupled with the pins 138b of the cartridge 120.

In step 580, the analyzer console can begin rotatory reciprocation of the pins in relation to the cups of the cartridge. For example, this step is exemplified above in reference to FIG. 10C.

In step 590, the analyzer console can heat the cartridge. In some implementations, the analyzer console may heat the cartridge to a predetermined temperature. In particular implementations, the analyzer console may maintain the cartridge at the predetermined temperature. For example, in some implementations the predetermined temperature may be about 35° C. to about 40° C., and preferably about 37° C.

In step 600, the analyzer console provides a prompt to couple a blood sample container to the cartridge. This prompt may be provided, for example upon the successful completion of one or more steps, or upon the successful verification of one or more conditions, or both. For example, this prompt may be provided upon the cartridge's successful attainment of the predetermined temperature as per step 590, among other things. The prompt may be provided via the user interface of the analyzer console. For example, the prompt may be a visual message displayed on a touchscreen monitor of the analyzer console. An audible prompt may be provided in some implementations.

In step 610, the analyzer console may optionally detect the presence of blood in the cartridge. Such detection may be performed, for example, using one or more IR sensors of the analyzer console. The detection of blood in the cartridge in this step can indicate that a blood sample container was successfully coupled to the cartridge.

In step 620, the analyzer console can provide a prompt to "start" testing. In some implementations, the prompt to "start" testing may be provided on the basis of the successful completion of one or more steps, or upon the successful verification of one or more conditions, or both. The prompt may be provided via the user interface of the analyzer console. For example, the prompt may be a visual message displayed on a touchscreen monitor of the analyzer console. In some embodiments, the touchscreen can receive a user input to start the testing.

In step 630, the analyzer console can cause blood to flow from the sample container into the cartridge. In some implementations, a vacuum source of the analyzer console is used to cause blood flow into the cartridge. In some implementations, an air pressure source of the analyzer console is used to cause blood flow into the cartridge. The analyzer console may also actuate various valves or vents to control the blood flow within the cartridge (e.g., refer to FIGS. 8A-8H).

In step 640, the analyzer console can induce agitation to assist with the dissolving of reagents in the blood contained within the cartridge. This step is exemplified above in regard to the horizontal reciprocation of the magnet shuttle with its one or more magnets that are magnetically coupled with mixing elements of the cartridge 120, causes movement of the mixing elements within the cartridge 120 to encourage the reagent beads to dissolve in the blood contained within the mixing chambers 134a-e.

In step 650, thromboelastometry testing is started. For example, the analyzer console can begin to analyze the data produced the thromboelastometry assemblies in regard to the reciprocating rotation of the shafts that are coupled with the pins 138a-e located in the cups 136a-e of the cartridge (refer to FIGS. 8A-8H). In some implementations, the analyzer console may begin to analyze the data produced by some of the thromboelastometry assemblies prior to beginning to analyze the data produced by others of the thromboelastometry assemblies. For example, as described above in reference to FIGS. 8A-8H, the analyzer console may begin to first analyze the data produced by the thromboelastometry assembly pertaining to cup 136e. Subsequently, the analyzer console may begin to analyze the data produced by the thromboelastometry assembly pertaining to cup 136d, and so on.

In step 660, the analyzer console displays the results of the thromboelastometry. Such results may be displayed concurrently with the performance of the testing and at the completion of the testing. The results can be displayed via the user interface of the analyzer console, such as on the touchscreen display. The results can be displayed using qualitative graphical representations and quantitative parameters.

In step 670, the analyzer console can unclamp the cartridge at the cessation of the testing. In some cases, such cessation may be initiated by a user input to the analyzer console to stop the testing, or by the completion of the test assays, or by the expiration of a time-based parameter. The unclamping may be performed, for example, by the horizontal translation of the moveable block sub-assembly. After the unclamping, the cartridge can be removed from the analyzer console.

A number of embodiments of the invention have been described. Nevertheless, it will be understood that various modifications may be made without departing from the spirit and scope of the invention. Accordingly, other embodiments are within the scope of the following claims.

What is claimed is:

1. A cartridge device for a measuring system for measuring viscoelastic characteristics of a sample liquid, the cartridge device comprising:
   a measuring chamber formed therein configured to contain a predetermined amount of the sample liquid; and
   a mixing chamber formed therein and in fluid connection with the measuring chamber for receiving the predetermined amount of the sample liquid, flowed from the measuring chamber, the mixing chamber comprising:
   a retaining element comprising an array of posts crossing a flow direction from the measuring chamber into the mixing chamber and coupled to a wall within the mixing chamber, the array of posts of the retaining element restricting movement of a set of reagent beads within the mixing chamber, individually separating each of the set of reagents beads from other reagent beads of the set of reagent beads, and separating the set of reagents beads from a mixing element retained within the mixing chamber.

2. The cartridge device of claim 1, wherein the sample fluid entirely submerges the set of reagent beads below a predetermined sample liquid fill level in the mixing chamber and fluidly couples the set of reagent beads and the mixing element.

3. The cartridge device of claim 1, wherein the retaining element is configured to prevent interaction of the mixing element and the reagent bead.

4. The cartridge device of claim 1, wherein the retaining element is configured to prevent interaction of the reagent bead with another reagent bead in the mixing chamber.

5. The cartridge device of claim 1, wherein the retaining element is configured to maintain the reagent bead at a predetermined vertical location in the mixing chamber.

6. The cartridge device of claim 5, wherein the predetermined vertical location is above the fill level of solution in the mixing chamber.

7. The cartridge device of claim 1, wherein the retaining element comprises a barrier.

8. The cartridge device of claim 1, wherein the retaining element comprises an inward protrusion or an outward protrusion in the wall of the mixing chamber.

9. The cartridge device of claim 1, wherein the retaining element comprises a compartment for holding at least one reagent bead.

10. The cartridge device of claim 1, wherein the mixing chamber retains a dry reagent near an exit of the sample liquid.

11. The cartridge device of claim 1, wherein the mixing chamber further comprises a reagent deposited on a wall of the mixing chamber.

12. The cartridge device of claim 10, wherein the reagent is below the fill level of the mixing chamber.

13. The cartridge device of claim 10, wherein the reagent is deposited on the wall of the mixing in the form of a dissolvable thin film.

14. The cartridge device of claim 1, wherein the sample liquid is a blood sample.

15. The cartridge device of claim 1, further comprising a first duct connecting the measuring chamber to the mixing chamber.

16. The cartridge device of claim 15, wherein the first duct comprises a reagent bead disposed therein.

17. The cartridge device of claim 15, wherein the first duct comprises a second retaining element configured to retain a reagent in the first duct.

18. The cartridge device of claim 17, wherein the second retaining element is configured to allow sample to flow through the first duct across the reagent.

19. The cartridge device of claim 1, further comprising a testing chamber comprising a probe element arranged therein, the probe element configured to perform a test on the sample liquid received from the mixing chamber.

20. The cartridge device of claim 19, wherein the testing chamber measures the viscoelastic characteristics of the sample liquid.

21. The cartridge device of claim 19, wherein the probe element is movable within the testing chamber for measuring viscoelastic characteristics of the sample liquid.

22. The cartridge device of claim 19, further comprising a second duct connecting the testing chamber to the mixing chamber, the testing chamber configured for receiving a sample liquid from the mixing chamber, the sample liquid comprising dissolved reagent.

23. The cartridge device of claim 22, further comprising a dry reagent deposited in the second duct connecting the testing chamber to the mixing chamber.

24. The cartridge device of claim 19, wherein the cartridge device is attachable to an interface element of a measuring system for measuring viscoelastic characteristics of a sample liquid, the measuring system comprising:
   a shaft rotatably supported by the interface element to be rotated by drive means, the probe element of the testing chamber engageable with the shaft;
   a detector engaging with the shaft for measuring viscoelastic characteristics of the sample liquid in contact with the probe element; and
   a controller to control the measuring system.

25. The measuring system of claim 24, wherein the probe element is movable within the testing chamber of the cartridge device for measuring viscoelastic characteristics of the sample liquid.

26. The measuring system of claim 24, wherein the sample liquid is a blood sample.

27. A method for measuring viscoelastic characteristics of a sample liquid by the measuring system of claim 24, comprising:
   providing the cartridge device having the testing chamber with the probe element arranged therein;
   attaching the cartridge device to the interface element, the shaft being inserted into the probe element;
   filling the testing chamber of the cartridge device with the sample liquid;
   rotating the shaft in an oscillating motion around a rotation axis; and
   measuring viscoelastic characteristics of the sample liquid by detecting the rotation of the shaft by the detecting means.

28. A method of mixing a sample liquid with a reagent for measuring viscoelastic characteristics of the sample liquid, comprising:
   providing a cartridge device of claim 1 comprising a sample liquid in the measuring chamber; and flowing the sample liquid to the mixing chamber, thereby contacting the sample liquid with the reagent bead that is retained in place by the retaining element and is retained such that the reagent bead is below a sample liquid fill level for the mixing chamber, wherein the sample liquid dissolves the reagent bead, the reagent in the reagent bead mixing with the sample liquid.

29. The method of claim 28, wherein the sample liquid is a blood sample.

30. The method of claim 28, further comprising using an external magnet to cause movement of the mixing element, thereby agitating the solution to facilitate dissolution of the reagent bead into the sample liquid.

* * * * *